US011432949B2

(12) United States Patent
Dagan et al.

(10) Patent No.: US 11,432,949 B2
(45) Date of Patent: Sep. 6, 2022

(54) ANTENNA POSTS

(71) Applicant: Enopace Biomedical Ltd., Caesarea Industrial Park (IL)

(72) Inventors: Amir Dagan, Kibbutz Megiddo (IL); Yoav Katz, Binyamina (IL); Fabian Lipperman, Kfar Saba (IL); Tanhum Feld, Moshav Merhavya (IL); Nadav Peleg, Zur Moshe (IL); Gal Ariav, Givat Ada (IL)

(73) Assignee: Enopace Biomedical Ltd., Caesarea Industrial Park (IL)

( * ) Notice: Subject to any disclaimer, the term of this patent is extended or adjusted under 35 U.S.C. 154(b) by 145 days.

(21) Appl. No.: 16/864,762

(22) Filed: May 1, 2020

(65) Prior Publication Data
US 2020/0253754 A1 Aug. 13, 2020

Related U.S. Application Data

(63) Continuation of application No. 15/034,803, filed as application No. PCT/IL2014/050972 on Nov. 6, 2014, now Pat. No. 10,779,965.
(Continued)

(51) Int. Cl.
*A61F 2/82* (2013.01)
*A61N 1/05* (2006.01)
(Continued)

(52) U.S. Cl.
CPC .............. *A61F 2/82* (2013.01); *A61N 1/0558* (2013.01); *A61N 1/36114* (2013.01);
(Continued)

(58) Field of Classification Search
CPC ......... A61F 2/07–2002/077; A61F 2/24–2475; A61F 2/82–945; A61F 2250/0001–0002
See application file for complete search history.

(56) References Cited

U.S. PATENT DOCUMENTS 3,650,277 A 3/1972 Sjostrand et al.
3,661,148 A 5/1972 Kolin
(Continued)

FOREIGN PATENT DOCUMENTS

CN 103079497 A 5/2013
EP 0 109 935 5/1984
(Continued)

OTHER PUBLICATIONS

U.S. Appl. No. 61/900,461, filed Nov. 6, 2013.
(Continued)

*Primary Examiner* — Rebecca S Preston
(74) *Attorney, Agent, or Firm* — Locke Lord LLP; Joshua L. Jones; Gabrielle L. Gelozin

(57) ABSTRACT

Apparatus and methods are described, including a stent configured to be placed in a lumen. The stent includes a generally cylindrical stent body including a plurality of struts, at least one electrode post protruding from the stent body, and a plurality of antenna posts protruding longitudinally from an end of the stent body. The antenna posts are longitudinally separated from the electrode post. An antenna is disposed annularly on the antenna posts, such that the antenna posts separate the antenna from the end of the stent body, and at least one electrode is coupled to the stent by being placed on the electrode post. Additional embodiments are also described.

7 Claims, 6 Drawing Sheets

Related U.S. Application Data

(60) Provisional application No. 61/900,461, filed on Nov. 6, 2013.

(51) Int. Cl.
    *A61N 1/36*    (2006.01)
    *A61N 1/372*    (2006.01)
    *A61N 1/375*    (2006.01)
    *A61N 1/39*    (2006.01)
    *A61F 2/915*    (2013.01)
    *A61F 2/88*    (2006.01)
    *A61F 2/844*    (2013.01)

(52) U.S. Cl.
CPC ..... *A61N 1/37205* (2013.01); *A61N 1/37229* (2013.01); *A61N 1/37516* (2017.08); *A61N 1/3962* (2013.01); *A61F 2/844* (2013.01); *A61F 2/88* (2013.01); *A61F 2/915* (2013.01); *A61F 2002/825* (2013.01); *A61F 2002/91525* (2013.01); *A61F 2002/91533* (2013.01); *A61F 2002/91558* (2013.01); *A61F 2002/91566* (2013.01); *A61F 2210/0014* (2013.01); *A61F 2220/0075* (2013.01); *A61F 2250/0001* (2013.01); *A61F 2250/0002* (2013.01); *A61F 2250/0029* (2013.01); *A61F 2250/0043* (2013.01); *A61N 1/36117* (2013.01); *A61N 1/375* (2013.01); *A61N 1/3756* (2013.01)

(56) References Cited

U.S. PATENT DOCUMENTS

| | | | |
|---|---|---|---|
| 4,154,227 | A | 5/1979 | Krause et al. |
| 4,201,219 | A | 5/1980 | Bozal |
| 4,474,630 | A | 10/1984 | Planck et al. |
| 4,692,148 | A | 9/1987 | Kantrowitz et al. |
| 4,791,931 | A | 12/1988 | Slate |
| 4,809,681 | A | 3/1989 | Kantrowitz et al. |
| 4,821,723 | A | 4/1989 | Baker, Jr. et al. |
| 4,848,352 | A | 7/1989 | Pohndorf |
| 4,938,766 | A | 7/1990 | Jarvik |
| 5,192,271 | A | 3/1993 | Kalb et al. |
| 5,199,428 | A | 4/1993 | Obel et al. |
| 5,224,491 | A | 7/1993 | Mehra |
| 5,265,011 | A | 11/1993 | O'Rourke |
| 5,265,601 | A | 11/1993 | Mehra |
| 5,306,292 | A | 4/1994 | Lindegren |
| 5,324,323 | A | 6/1994 | Bui |
| 5,330,507 | A | 7/1994 | Schwartz |
| 5,372,573 | A | 12/1994 | Habib |
| 5,411,031 | A | 5/1995 | Yomtov |
| 5,423,871 | A | 6/1995 | Hoegnelid et al. |
| 5,458,626 | A | 10/1995 | Krause |
| 5,487,760 | A | 1/1996 | Villafana |
| 5,540,730 | A | 7/1996 | Terry et al. |
| 5,571,150 | A | 11/1996 | Wernicke et al. |
| 5,612,314 | A | 3/1997 | Stamler et al. |
| 5,645,839 | A | 7/1997 | Chobanian et al. |
| 5,649,966 | A | 7/1997 | Noren et al. |
| 5,651,378 | A | 7/1997 | Matheny et al. |
| 5,669,924 | A | 9/1997 | Shaknovich |
| 5,690,681 | A | 11/1997 | Geddes et al. |
| 5,707,400 | A | 1/1998 | Terry, Jr. |
| 5,735,887 | A | 4/1998 | Barreras et al. |
| 5,762,599 | A | 6/1998 | Sohn |
| 5,782,774 | A | 7/1998 | Shmulewitz |
| 5,800,464 | A | 9/1998 | Kieval |
| 5,800,502 | A | 9/1998 | Boutos |
| 5,814,089 | A | 9/1998 | Stokes et al. |
| 5,873,865 | A | 2/1999 | Horzewski et al. |
| 5,900,433 | A | 5/1999 | Igo et al. |
| 5,902,712 | A | 5/1999 | Burns et al. |
| 5,904,711 | A | 5/1999 | Geddes et al. |
| 5,904,712 | A | 5/1999 | Axelgaard |
| 5,906,641 | A | 5/1999 | Thompson et al. |
| 5,913,876 | A | 6/1999 | Taylor et al. |
| 5,925,061 | A | 7/1999 | Ogi et al. |
| 5,935,077 | A | 8/1999 | Ogle |
| 5,948,006 | A | 9/1999 | Mann |
| 5,967,986 | A | 10/1999 | Cimochowski et al. |
| 5,994,444 | A | 11/1999 | Trescony et al. |
| 5,997,563 | A | 12/1999 | Kretzers |
| 6,014,589 | A | 1/2000 | Farley et al. |
| 6,023,640 | A | 2/2000 | Ross |
| 6,029,091 | A | 2/2000 | De La Rama et al. |
| 6,038,485 | A | 3/2000 | Axelgaard |
| 6,053,873 | A | 4/2000 | Govari |
| 6,058,331 | A | 5/2000 | King |
| 6,073,048 | A | 6/2000 | Kieval et al. |
| 6,086,527 | A | 7/2000 | Talpade |
| 6,104,956 | A | 8/2000 | Naritoku et al. |
| 6,106,477 | A | 8/2000 | Miesel et al. |
| 6,120,520 | A | 9/2000 | Saadat |
| 6,141,587 | A | 10/2000 | Mower |
| 6,178,349 | B1 | 1/2001 | Kieval |
| 6,200,259 | B1 | 3/2001 | March |
| 6,201,991 | B1 | 3/2001 | Chekanov |
| 6,231,516 | B1 | 5/2001 | Keilman et al. |
| 6,245,103 | B1 | 6/2001 | Stinson |
| 6,246,911 | B1 | 6/2001 | Seligman |
| 6,270,524 | B1 | 8/2001 | Kim |
| 6,273,910 | B1 | 8/2001 | Limon |
| 6,277,078 | B1 | 8/2001 | Porat et al. |
| 6,292,695 | B1 | 9/2001 | Webster et al. |
| 6,317,631 | B1 | 11/2001 | Ben-Haim et al. |
| 6,339,725 | B1 | 1/2002 | Naritoku et al. |
| 6,347,247 | B1 | 2/2002 | Dev et al. |
| 6,411,845 | B1 | 6/2002 | Mower |
| 6,418,348 | B1 | 7/2002 | Witte |
| 6,423,084 | B1 | 7/2002 | St. Germain |
| 6,440,059 | B1 | 8/2002 | Haas et al. |
| 6,445,953 | B1 | 9/2002 | Bulkes |
| 6,463,323 | B1 | 10/2002 | Conrad et al. |
| 6,473,644 | B1 | 10/2002 | Terry et al. |
| 6,480,747 | B2 | 11/2002 | Schmidt |
| 6,485,524 | B2 | 11/2002 | Strecker |
| 6,496,732 | B1 | 12/2002 | Wallace |
| 6,522,926 | B1 | 2/2003 | Kieval et al. |
| 6,532,388 | B1 | 3/2003 | Hill et al. |
| 6,582,461 | B1 | 6/2003 | Burmeister et al. |
| 6,611,715 | B1 | 8/2003 | Boveja |
| 6,615,085 | B1 | 9/2003 | Boveja |
| 6,616,613 | B1 | 9/2003 | Goodman |
| 6,616,624 | B1 | 9/2003 | Kieval et al. |
| 6,622,041 | B2 | 9/2003 | Terry, Jr. et al. |
| 6,626,935 | B1 | 9/2003 | Ainsworth et al. |
| 6,631,296 | B1 | 10/2003 | Parramon et al. |
| 6,632,991 | B2 | 10/2003 | Chen |
| 6,647,287 | B1 | 11/2003 | Peel, III |
| 6,656,960 | B2 | 12/2003 | Puskas |
| 6,668,191 | B1 | 12/2003 | Boveja |
| 6,682,480 | B1 | 1/2004 | Habib et al. |
| 6,721,603 | B2 | 4/2004 | Zabara et al. |
| 6,735,474 | B1 | 5/2004 | Loeb |
| 6,770,088 | B1 | 8/2004 | Jang |
| 6,810,286 | B2 | 10/2004 | Donovan et al. |
| 6,824,561 | B2 | 11/2004 | Soykan et al. |
| 6,845,267 | B2 | 1/2005 | Harrison et al. |
| 6,850,801 | B2 | 2/2005 | Kieval et al. |
| 6,865,416 | B2 | 3/2005 | Dev et al. |
| 6,871,092 | B2 | 3/2005 | Piccone |
| 6,885,895 | B1 | 4/2005 | Whitehurst et al. |
| 6,934,583 | B2 | 8/2005 | Weinberg et al. |
| 6,939,345 | B2 | 9/2005 | KenKnight et al. |
| 6,947,792 | B2 | 9/2005 | Ben-Haim et al. |
| 6,985,774 | B2 | 1/2006 | Kieval et al. |
| 7,044,981 | B2 | 5/2006 | Liu et al. |
| 7,062,318 | B2 | 6/2006 | Ben-Haim et al. |
| 7,076,307 | B2 | 7/2006 | Boveja et al. |
| 7,079,901 | B1 | 7/2006 | Loftin et al. |
| 7,082,336 | B2 | 7/2006 | Ransbury et al. |
| 7,090,648 | B2 | 8/2006 | Sackner et al. |
| 7,123,961 | B1 | 10/2006 | Kroll et al. |

(56) References Cited

U.S. PATENT DOCUMENTS

| | | |
|---|---|---|
| 7,149,574 B2 | 12/2006 | Yun et al. |
| 7,158,832 B2 | 1/2007 | Kieval et al. |
| 7,167,751 B1 | 1/2007 | Whitehurst et al. |
| 7,191,007 B2 | 3/2007 | Desai et al. |
| 7,191,012 B2 | 3/2007 | Boveja et al. |
| 7,201,719 B2 | 4/2007 | Feliss et al. |
| 7,206,637 B2 | 4/2007 | Salo |
| 7,225,019 B2 | 5/2007 | Jahns et al. |
| 7,228,167 B2 | 6/2007 | Kara et al. |
| 7,229,403 B2 | 6/2007 | Schock et al. |
| 7,263,405 B2 | 8/2007 | Boveja et al. |
| 7,269,457 B2 | 9/2007 | Shafer et al. |
| 7,277,761 B2 | 10/2007 | Shelchuk |
| 7,291,113 B2 | 11/2007 | Satoh et al. |
| 7,292,886 B1 | 11/2007 | Kroll |
| 7,299,091 B2 | 11/2007 | Barrett et al. |
| 7,321,793 B2 | 1/2008 | Ben Ezra et al. |
| 7,363,076 B2 | 4/2008 | Yun et al. |
| 7,367,970 B2 | 5/2008 | Govari et al. |
| 7,389,149 B2 | 6/2008 | Rossing et al. |
| 7,395,119 B2 | 7/2008 | Hagen et al. |
| 7,444,183 B2 | 10/2008 | Knudson et al. |
| 7,452,334 B2 | 11/2008 | Gianchandani |
| 7,471,986 B2 | 12/2008 | Hatlestad |
| 7,476,200 B2 | 1/2009 | Tal |
| 7,480,532 B2 | 1/2009 | Kieval et al. |
| 7,486,991 B2 | 2/2009 | Libbus et al. |
| 7,499,747 B2 | 3/2009 | Kieval et al. |
| 7,499,748 B2 | 3/2009 | Moffitt et al. |
| 7,502,650 B2 | 3/2009 | Kieval |
| 7,519,421 B2 | 4/2009 | Denker et al. |
| 7,532,932 B2 | 5/2009 | Denker et al. |
| 7,555,344 B2 | 6/2009 | Maschino et al. |
| 7,561,918 B2 | 7/2009 | Armstrong et al. |
| 7,570,999 B2 | 8/2009 | Libbus et al. |
| 7,613,511 B2 | 11/2009 | Wu et al. |
| 7,613,515 B2 | 11/2009 | Knudson et al. |
| 7,616,997 B2 | 11/2009 | Kieval et al. |
| 7,617,003 B2 | 11/2009 | Caparso et al. |
| 7,623,926 B2 | 11/2009 | Rossing et al. |
| 7,634,315 B2 | 12/2009 | Cholette |
| 7,706,875 B2 | 4/2010 | Buras et al. |
| 7,706,884 B2 | 4/2010 | Libbus |
| 7,706,886 B2 | 4/2010 | Morimoto et al. |
| 7,715,915 B1 | 5/2010 | Ryu et al. |
| 7,720,547 B2 | 5/2010 | Denker et al. |
| 7,725,194 B2 | 5/2010 | Klostermann et al. |
| 7,738,961 B2 | 6/2010 | Sharma |
| 7,747,302 B2 | 6/2010 | Milledge |
| 7,765,000 B2 | 7/2010 | Zhang et al. |
| 7,765,008 B2 | 7/2010 | Ben-Haim et al. |
| 7,769,446 B2 | 8/2010 | Moffitt et al. |
| 7,780,719 B2 | 8/2010 | Killion et al. |
| 7,801,604 B2 | 9/2010 | Brockway et al. |
| 7,811,221 B2 | 10/2010 | Gross |
| 7,813,805 B1 | 10/2010 | Farazi |
| 7,813,812 B2 | 10/2010 | Kieval et al. |
| 7,826,899 B1 | 11/2010 | Ryu et al. |
| 7,840,282 B2 | 11/2010 | Williams et al. |
| 7,848,820 B2 | 12/2010 | Abrahamson |
| 7,856,273 B2 | 12/2010 | Maschino et al. |
| 7,860,566 B2 | 12/2010 | Mazgalev et al. |
| 7,869,870 B1 | 1/2011 | Farazi |
| 7,881,782 B2 | 2/2011 | Libbus et al. |
| 7,881,792 B1 | 2/2011 | Farazi |
| 7,894,902 B2 | 2/2011 | Rom et al. |
| 7,899,554 B2 | 3/2011 | Williams et al. |
| 7,949,400 B2 | 5/2011 | Kieval et al. |
| 7,991,474 B2 | 8/2011 | Aldrich et al. |
| 8,046,085 B2 | 10/2011 | Knudson et al. |
| 8,065,019 B2 | 11/2011 | Marnfeldt et al. |
| 8,086,314 B1 | 12/2011 | Kieval |
| 8,095,218 B2 | 1/2012 | Gross et al. |
| 8,121,692 B2 | 2/2012 | Haefner et al. |
| 8,131,362 B2 | 3/2012 | Moffitt et al. |
| 8,150,508 B2 | 4/2012 | Craig |
| 8,160,701 B2 | 4/2012 | Zhao et al. |
| 8,175,705 B2 | 5/2012 | Libbus |
| 8,224,437 B2 | 7/2012 | Kieval et al. |
| 8,244,378 B2 | 8/2012 | Bly et al. |
| 8,249,705 B1 | 8/2012 | Kieval et al. |
| 8,290,595 B2 | 10/2012 | Kieval et al. |
| 8,386,038 B2 | 2/2013 | Bianchi et al. |
| 8,391,970 B2 | 3/2013 | Tracey et al. |
| 8,406,868 B2 | 3/2013 | Buschman et al. |
| 8,442,639 B2 | 5/2013 | Walker et al. |
| 8,449,472 B2 | 5/2013 | Ryu et al. |
| 8,457,743 B2 | 6/2013 | Gollasch et al. |
| 8,457,748 B2 | 6/2013 | Lange |
| 8,463,392 B2 | 6/2013 | Aghassian |
| 8,467,884 B2 | 6/2013 | Chen et al. |
| 8,478,414 B2 | 7/2013 | Kieval et al. |
| 8,498,704 B2 | 7/2013 | Shuros et al. |
| 8,504,161 B1 | 8/2013 | Kornet et al. |
| 8,509,919 B2 | 8/2013 | Yoo et al. |
| 8,521,293 B2 | 8/2013 | Anderson et al. |
| 8,538,535 B2 | 9/2013 | Gross |
| 8,538,542 B2 | 9/2013 | Knudson et al. |
| 8,560,076 B2 | 10/2013 | Kieval et al. |
| 8,571,654 B2 | 10/2013 | Libbus et al. |
| 8,571,664 B2 | 10/2013 | Anderson et al. |
| 8,577,458 B1 | 11/2013 | Libbus et al. |
| 8,577,548 B2 | 11/2013 | Miller et al. |
| 8,600,505 B2 | 12/2013 | Libbus et al. |
| 8,600,511 B2 | 12/2013 | Yared et al. |
| 8,600,521 B2 | 12/2013 | Armstrong et al. |
| 8,606,359 B2 | 12/2013 | Rossing et al. |
| 8,612,014 B2 | 12/2013 | Rahman et al. |
| 8,620,422 B2 | 12/2013 | Kieval et al. |
| 8,620,450 B2 | 12/2013 | Tockman et al. |
| 8,626,290 B2 | 1/2014 | Dagan |
| 8,626,299 B2 | 1/2014 | Gross et al. |
| 8,630,709 B2 | 1/2014 | Libbus et al. |
| 8,634,927 B2 | 1/2014 | Olson et al. |
| 8,634,928 B1 | 1/2014 | O'Driscoll et al. |
| 8,639,327 B2 | 1/2014 | Zhou et al. |
| 8,639,339 B2 | 1/2014 | Bange et al. |
| 8,644,928 B2 | 2/2014 | Takata |
| 8,660,666 B2 | 2/2014 | Craig |
| 8,663,103 B2 | 3/2014 | Causey et al. |
| 8,670,835 B2 | 3/2014 | Park et al. |
| 8,692,717 B2 | 4/2014 | Friedman |
| 8,700,145 B2 | 4/2014 | Kilgard et al. |
| 8,700,157 B2 | 4/2014 | Goetz et al. |
| 8,700,173 B2 | 4/2014 | Edlund |
| 8,706,223 B2 | 4/2014 | Zhou et al. |
| 8,712,531 B2 | 4/2014 | Kieval et al. |
| 8,729,129 B2 | 5/2014 | Tracey et al. |
| 8,731,663 B2 | 5/2014 | Bianchi et al. |
| 8,738,126 B2 | 5/2014 | Craig |
| 8,744,586 B2 | 6/2014 | Georgakopoulos et al. |
| 8,755,907 B2 | 6/2014 | Kieval et al. |
| 8,788,028 B2 | 7/2014 | Kumar et al. |
| 8,788,066 B2 | 7/2014 | Cates et al. |
| 8,805,513 B2 | 8/2014 | Libbus |
| 8,818,508 B2 | 8/2014 | Scheiner |
| 8,818,524 B2 | 8/2014 | Hincapie et al. |
| 8,880,185 B2 | 11/2014 | Hastings et al. |
| 8,929,990 B2 | 1/2015 | Moffitt et al. |
| 9,526,637 B2 | 12/2016 | Dagan et al. |
| 2001/0044434 A1 | 11/2001 | Lee et al. |
| 2002/0016615 A1 | 2/2002 | Dev |
| 2002/0026228 A1 | 2/2002 | Schauerte |
| 2002/0032468 A1 | 3/2002 | Hill |
| 2002/0055764 A1 | 5/2002 | Malonek et al. |
| 2002/0077554 A1 | 6/2002 | Schwartz |
| 2002/0089458 A1 | 7/2002 | Allen et al. |
| 2002/0103454 A1 | 8/2002 | Sackner et al. |
| 2002/0161377 A1 | 10/2002 | Rabkin |
| 2002/0169413 A1 | 11/2002 | Keren et al. |
| 2002/0198571 A1 | 12/2002 | Puskas |
| 2003/0036773 A1 | 2/2003 | Whitehurst et al. |
| 2003/0050683 A1 | 3/2003 | Boutos |
| 2003/0055465 A1 | 3/2003 | Ben-Haim et al. |

(56) References Cited

U.S. PATENT DOCUMENTS

| | | |
|---|---|---|
| 2003/0055466 A1 | 3/2003 | Ben-Haim et al. |
| 2003/0055467 A1 | 3/2003 | Ben-Haim et al. |
| 2003/0060858 A1 | 3/2003 | Kieval et al. |
| 2003/0109914 A1 | 6/2003 | Westlund et al. |
| 2003/0130715 A1 | 10/2003 | Boutos |
| 2003/0199806 A1 | 10/2003 | Kieval |
| 2003/0204206 A1 | 10/2003 | Padua et al. |
| 2004/0010303 A1 | 1/2004 | Bolea et al. |
| 2004/0019364 A1 | 1/2004 | Kieval et al. |
| 2004/0039417 A1 | 2/2004 | Soykan et al. |
| 2004/0044393 A1 | 3/2004 | Yarden |
| 2004/0054384 A1 | 3/2004 | Nachum |
| 2004/0064090 A1 | 4/2004 | Keren |
| 2004/0082948 A1 | 4/2004 | Stewart et al. |
| 2004/0015205 A1 | 6/2004 | Bradley |
| 2004/0106954 A1 | 6/2004 | Whitehurst et al. |
| 2004/0106976 A1 | 6/2004 | Bailey et al. |
| 2004/0111006 A1 | 6/2004 | Alferness |
| 2004/0133240 A1 | 7/2004 | Adams |
| 2004/0162590 A1 | 8/2004 | Whitehurst et al. |
| 2004/0210261 A1 | 10/2004 | King et al. |
| 2004/0254616 A1 | 12/2004 | Rossing et al. |
| 2005/0027346 A1 | 2/2005 | Arkusz et al. |
| 2005/0033407 A1 | 2/2005 | Weber et al. |
| 2005/0049680 A1 | 3/2005 | Fischell et al. |
| 2005/0049686 A1 | 3/2005 | Gray et al. |
| 2005/0065592 A1 | 3/2005 | Holzer |
| 2005/0090867 A1 | 4/2005 | Lapanashvili |
| 2005/0096702 A1* | 5/2005 | Denker .......... A61N 1/372 607/9 |
| 2005/0096710 A1 | 5/2005 | Kieval et al. |
| 2005/0143785 A1 | 6/2005 | Libbus |
| 2005/0143789 A1 | 6/2005 | Whitehurst |
| 2005/0149130 A1 | 7/2005 | Libbus |
| 2005/0149132 A1 | 7/2005 | Libbus |
| 2005/0149155 A1 | 7/2005 | Scheiner et al. |
| 2005/0149170 A1 | 7/2005 | Tassel et al. |
| 2005/0209652 A1 | 9/2005 | Whitehurst et al. |
| 2005/0233962 A1 | 10/2005 | Lue et al. |
| 2005/0240229 A1 | 10/2005 | Whitehurst et al. |
| 2005/0251212 A1 | 11/2005 | Kieval et al. |
| 2005/0283184 A1 | 12/2005 | Gilson et al. |
| 2005/0288651 A1 | 12/2005 | VanTassel et al. |
| 2006/0004417 A1 | 1/2006 | Rossing et al. |
| 2006/0004420 A1 | 1/2006 | Rossing et al. |
| 2006/0004430 A1 | 1/2006 | Rossing et al. |
| 2006/0074453 A1 | 4/2006 | Kieval et al. |
| 2006/0100668 A1 | 5/2006 | Ben-David et al. |
| 2006/0111626 A1 | 5/2006 | Rossing et al. |
| 2006/0149124 A1 | 7/2006 | Forsell |
| 2006/0149345 A1 | 7/2006 | Boggs, II et al. |
| 2006/0167540 A1 | 7/2006 | Masters et al. |
| 2006/0173507 A1 | 8/2006 | Mrva et al. |
| 2006/0217588 A1 | 9/2006 | Gross et al. |
| 2006/0217772 A1 | 9/2006 | Libbus et al. |
| 2006/0229677 A1 | 10/2006 | Moffitt et al. |
| 2006/0259085 A1 | 11/2006 | Zhang et al. |
| 2006/0265038 A1 | 11/2006 | Hagen et al. |
| 2006/0276844 A1 | 12/2006 | Alon et al. |
| 2006/0287705 A1 | 12/2006 | Weber |
| 2006/0293712 A1 | 12/2006 | Kieval et al. |
| 2007/0021673 A1 | 1/2007 | Arbel et al. |
| 2007/0021786 A1 | 1/2007 | Parnis et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027496 A1 | 2/2007 | Parnis et al. |
| 2007/0038255 A1 | 2/2007 | Kieval et al. |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0049989 A1 | 3/2007 | Rossing et al. |
| 2007/0060972 A1 | 3/2007 | Kieval et al. |
| 2007/0100433 A1 | 5/2007 | Limon |
| 2007/0106340 A1 | 5/2007 | Bolea et al. |
| 2007/0142879 A1 | 6/2007 | Greenberg et al. |
| 2007/0150009 A1 | 6/2007 | Kveen et al. |
| 2007/0156179 A1 | 7/2007 | Karashurov |
| 2007/0156198 A1 | 7/2007 | Rossing et al. |
| 2007/0156201 A1 | 7/2007 | Rossing et al. |
| 2007/0167984 A1 | 7/2007 | Kieval et al. |
| 2007/0185540 A1 | 8/2007 | Ben-Haim et al. |
| 2007/0185542 A1 | 8/2007 | Bolea et al. |
| 2007/0185543 A1 | 8/2007 | Rossing et al. |
| 2007/0191904 A1 | 8/2007 | Libbus et al. |
| 2007/0196428 A1 | 8/2007 | Glauser et al. |
| 2007/0198064 A1 | 8/2007 | Lapanashvili et al. |
| 2007/0248676 A1 | 10/2007 | Stamler et al. |
| 2007/0248850 A1 | 10/2007 | Heller |
| 2007/0255379 A1 | 11/2007 | Williams et al. |
| 2007/0276270 A1 | 11/2007 | Tran |
| 2007/0276459 A1 | 11/2007 | Rossing et al. |
| 2007/0282385 A1 | 12/2007 | Rossing et al. |
| 2007/0288076 A1 | 12/2007 | Bulkes et al. |
| 2007/0293927 A1 | 12/2007 | Frank et al. |
| 2008/0004673 A1 | 1/2008 | Rossing et al. |
| 2008/0009916 A1 | 1/2008 | Rossing et al. |
| 2008/0009917 A1 | 1/2008 | Rossing et al. |
| 2008/0021336 A1 | 1/2008 | Dobak |
| 2008/0046016 A1 | 2/2008 | Ben-David et al. |
| 2008/0046054 A1 | 2/2008 | Hjelle et al. |
| 2008/0051767 A1 | 2/2008 | Rossing et al. |
| 2008/0051849 A1 | 2/2008 | Ben-Haim et al. |
| 2008/0058872 A1 | 3/2008 | Brockway et al. |
| 2008/0058889 A1 | 3/2008 | Ben-Haim et al. |
| 2008/0058891 A1 | 3/2008 | Ben-Haim et al. |
| 2008/0071363 A1 | 3/2008 | Tuval et al. |
| 2008/0077016 A1 | 3/2008 | Sparks et al. |
| 2008/0082137 A1 | 4/2008 | Kieval et al. |
| 2008/0097540 A1 | 4/2008 | Bolea et al. |
| 2008/0119898 A1 | 5/2008 | Ben-David |
| 2008/0119911 A1 | 5/2008 | Rosero |
| 2008/0132972 A1 | 6/2008 | Shuros et al. |
| 2008/0140167 A1 | 6/2008 | Hagen et al. |
| 2008/0147168 A1 | 6/2008 | Ransbury et al. |
| 2008/0154349 A1 | 6/2008 | Rossing et al. |
| 2008/0161865 A1 | 7/2008 | Hagen et al. |
| 2008/0161887 A1 | 7/2008 | Hagen et al. |
| 2008/0167690 A1 | 7/2008 | Cody et al. |
| 2008/0167693 A1 | 7/2008 | Kieval et al. |
| 2008/0167694 A1 | 7/2008 | Bolea et al. |
| 2008/0167696 A1 | 7/2008 | Cates et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0172104 A1 | 7/2008 | Kieval et al. |
| 2008/0177364 A1 | 7/2008 | Bolea et al. |
| 2008/0183254 A1 | 7/2008 | Bly et al. |
| 2008/0195174 A1 | 8/2008 | Walker et al. |
| 2008/0215117 A1 | 9/2008 | Gross |
| 2009/0005859 A1 | 1/2009 | Keilman |
| 2009/0036975 A1 | 2/2009 | Ward |
| 2009/0062874 A1 | 3/2009 | Tracey |
| 2009/0112285 A1 | 4/2009 | Cahan et al. |
| 2009/0160716 A1 | 6/2009 | Rhodes et al. |
| 2009/0171425 A1 | 7/2009 | Dahlberg |
| 2009/0198097 A1 | 8/2009 | Gross |
| 2009/0198308 A1 | 8/2009 | Gross et al. |
| 2009/0204170 A1 | 8/2009 | Hastings |
| 2009/0228078 A1 | 9/2009 | Zhang et al. |
| 2009/0248133 A1 | 10/2009 | Bloom et al. |
| 2009/0270951 A1 | 10/2009 | Kallmyer |
| 2010/0004650 A1 | 1/2010 | Ormsby et al. |
| 2010/0010556 A1 | 1/2010 | Zhao et al. |
| 2010/0016957 A1* | 1/2010 | Jager .......... A61K 9/0024 623/1.42 |
| 2010/0042186 A1 | 2/2010 | Ben David et al. |
| 2010/0052668 A1 | 3/2010 | Gleich |
| 2010/0076247 A1 | 3/2010 | Zilbershlag et al. |

(56) References Cited

U.S. PATENT DOCUMENTS

| | | |
|---|---|---|
| 2010/0094373 A1 | 4/2010 | Sharma |
| 2010/0211131 A1 | 8/2010 | Williams et al. |
| 2010/0249888 A1 | 9/2010 | Glenn et al. |
| 2010/0280568 A1 | 11/2010 | Bulkes et al. |
| 2010/0280593 A1 | 11/2010 | Richter |
| 2010/0305392 A1 | 12/2010 | Gross et al. |
| 2011/0106237 A1 | 5/2011 | Bonsignore et al. |
| 2011/0118773 A1 | 5/2011 | Gross et al. |
| 2011/0137370 A1 | 6/2011 | Gross et al. |
| 2011/0301670 A1 | 12/2011 | Gross |
| 2012/0003569 A1 | 1/2012 | Kawamura et al. |
| 2012/0035679 A1 | 2/2012 | Dagan et al. |
| 2012/0035711 A1 | 2/2012 | Gross et al. |
| 2012/0158081 A1 | 6/2012 | Gross et al. |
| 2012/0303112 A1 | 11/2012 | Armstrong et al. |
| 2013/0043736 A1 | 2/2013 | Zilbershlag |
| 2013/0123880 A1 | 5/2013 | Dagan et al. |
| 2013/0310629 A1 | 11/2013 | Lafontaine |
| 2013/0338748 A1 | 12/2013 | Dagan |
| 2014/0031607 A1 | 1/2014 | Zilbershlag et al. |
| 2014/0081154 A1 | 3/2014 | Toth |
| 2014/0180391 A1 | 6/2014 | Dagan et al. |
| 2016/0278951 A1 | 9/2016 | Dagan et al. |
| 2017/0065824 A1 | 3/2017 | Dagan et al. |

FOREIGN PATENT DOCUMENTS

| | | |
|---|---|---|
| EP | 0 791 341 | 8/1997 |
| WO | 99/026530 | 6/1999 |
| WO | 00/002501 | 1/2000 |
| WO | 02/26314 | 4/2002 |
| WO | 03/076008 | 9/2003 |
| WO | 03/082080 | 10/2003 |
| WO | 03/082403 | 10/2003 |
| WO | 04/014456 | 2/2004 |
| WO | 04/073484 | 9/2004 |
| WO | 05/032414 | 4/2005 |
| WO | 2005/065771 | 7/2005 |
| WO | 05/084389 | 9/2005 |
| WO | 05/097256 | 10/2005 |
| WO | 06/012033 | 2/2006 |
| WO | 06/012050 | 2/2006 |
| WO | 06/032902 | 3/2006 |
| WO | 06/041664 | 4/2006 |
| WO | 06/064503 | 6/2006 |
| WO | 06/089739 | 8/2006 |
| WO | 06/094273 | 9/2006 |
| WO | 2006/098928 | 9/2006 |
| WO | 06/123346 | 11/2006 |
| WO | 06/125163 | 11/2006 |
| WO | 07/013065 | 2/2007 |
| WO | 07/047152 | 4/2007 |
| WO | 07/064895 | 6/2007 |
| WO | 07/106533 | 9/2007 |
| WO | 07/113818 | 10/2007 |
| WO | 07/113833 | 10/2007 |
| WO | 07/114860 | 10/2007 |
| WO | 07/118090 | 10/2007 |
| WO | 07/136850 | 11/2007 |
| WO | 07/136851 | 11/2007 |
| WO | 08/039982 | 4/2008 |
| WO | 08/083120 | 7/2008 |
| WO | 08/083235 | 7/2008 |
| WO | 08/100390 | 8/2008 |
| WO | 2009/017647 | 2/2009 |
| WO | 09/095918 | 8/2009 |
| WO | 09/095920 | 8/2009 |
| WO | 10/118126 | 10/2010 |
| WO | 2012/017437 | 2/2012 |
| WO | 2012/085907 | 6/2012 |
| WO | 2013/035092 A2 | 3/2013 |
| WO | 2013030819 A1 | 3/2013 |
| WO | 2013/069020 | 5/2013 |
| WO | 2013/164829 | 11/2013 |

OTHER PUBLICATIONS

U.S. Appl. No. 15/034,803, filed May 5, 2016, published as 2016/0278951.

Evaluation of Cardiovascular Stents as Antennas for Implantable Wireless Applications, by Chow, IEEE Transactions on Microwave Theory and Techniques, vol. 57, No. 10, Oct. 2009.

An Office Action dated Mar. 15, 2012, which issued during the prosecution of U.S. Appl. No. 12/792,227.

An Office Action dated Aug. 9, 2011, which issued during the prosecution of U.S. Appl. No. 12/023,896.

Cardiovascular Stents as Antennas for Implantable Wireless Applications, by Ebrish, BMEN 5151, Apr. 29, 2010.

An Office Action dated Mar. 13, 2012, which issued during the prosecution of U.S. Appl. No. 12/023,896.

An Office Action dated Dec. 19, 2011, which issued during the prosecution of U.S. Appl. No. 11/995,904.

An Office Action dated Nov. 18, 2009, which issued during the prosecution of U.S. Appl. No. 12/023,900.

An International Search Report together with the Written Opinion both dated Dec. 19, 2011, which issued during the prosecution of Applicant's PCT/IL2011/000636.

An International Search Report dated Jan. 24, 2007, which issued during the prosecution of Applicant's PCT/IL06/00856.

An International Search Report and a Written Opinion both dated May 12, 2009, which issued during the prosecution of Applicant's PCT/IL09/00115.

An International Search Report and a Written Opinion both dated Jul. 13, 2009, which issued during the prosecution of Applicant's PCT/IL09/00117.

An International Preliminary Report on Patentability dated Jan. 24, 2007, which issued during the prosecution of Applicant's PCT/IL06/00856.

An International Preliminary Report on Patentability dated Aug. 3, 2010, which issued during the prosecution of Applicant's PCT/IL09/00117.

An International Preliminary Report on Patentability dated Aug. 3, 2010, which issued during the prosecution of Applicant's PCT/IL09/00115.

Taylor, The unequal influences of the left and right vagi on the control of the heart and pulmonary artery in the rattlesnake, Crotalus durissus, The Journal of Experimental Biology 212, pp. 145-151, 2009.

Hamilton, Coronary vascular sympathetic beta-receptor innervations,, American Journal of Physiology, vol. 230, No. 6, Jun. 1976.

An International Search Report and a Written Opinion both dated Mar. 5, 2013, which issued during the prosecution of Applicant's PCT/IL12/00336.

Matheny, Vagus nerve stimulation as a method to temporarily slow or arrest the heart, Ann Thorac Surg. Jun. 1997;63(6 Suppl):S28-9. Abstract only.

Lewis, Vagus nerve stimulation decreases left ventricular contractility in vivo in the human and pig heart, J Physiol. Jul. 15, 2001; 534(Pt 2): 547-552.

Laitinen, Am J, Sympathovagal balance is major determinant of short-term blood pressure variability in healthy subjects, Physiol Heart Circ Physiol 276:1245-1252, 1999.

Frost MC, Preparation and characterization of implantable sensors with nitric oxide release coatings, Microchemical Journal vol. 74 Issue: 3, Jun. 2003 pp. 277-288.

Baudrie, Am J, Optimal frequency ranges for extracting information on cardiovascular autonomic control from the blood pressure and pulse interval spectrograms in mice, Physiol Regul Integr Comp Physiol 292: R904-R912, 2007.

Kugiyama K, Nitric oxide activity is deficient in spasm arteries of patients with coronary spastic angina, Circulation 94:266-272 (1996).

Malpas, Neural influences on cardiovascular variability: possibilities and pitfalls,, Am J Physiol Heart Circ Physiol 282: H6-H20, 2002.

Shin Jae Ho, "Improving the biocompatibility of in vivo sensors via nitric oxide release,"Analyst, 2006, 131, 609-615.

Zhao et al., Loss of nitric oxide production in the coronary circulation after the development of dilated cardiomyopathy: a specific

(56) References Cited

OTHER PUBLICATIONS defect in the neural regulation of coronary blood flow, Clinical and Experimental Pharmacology and Physiology 23(8): 715-721 (1996).
Sherman et al., Blockade of nitric oxide synthesis reduces myocardial oxygen consumption in vivo, Circulation 95:1328-1334 (1997).
Schoenfisch et al., "Improving the thromboresistivity of chemical sensors via nitric oxide release: fabrication and in vivo evaluation of NO-releasing oxygen-sensing catheters", Anal. Chem., 72 (6), 1119-1126, 2000.
Paulus, "Beneficial effects of nitric oxide on cardiac diastolic function: the flip side of the coin", Heart Failure Review 5(4):337-344 (2000).
Web page relating to EndoSure® Wireless AAA Pressure Measurement System, manufactured by CardioMEMS, Inc. (downloaded on Nov. 20, 2010 from: http://www.cardiomems.com/content.asp?display=medical+mb&expand=ess.
Cheetah Medical Inc. manufactures the Cheetah Reliant, Jan. 23, 2008.
SULZER IntarTeraputic Inc. manufactures the IntraCoil® Self-Expanding Peripheral Sent (IntraCoil® Sent), Jun. 28, 2002.
Hayashida et al., "Comparison of neurogenic contraction and relaxation in canine corpus cavernosum and penile artery and vein", J. Pharmacol. 72:231-240 (1996), p. 232 col. 2, para. 1; p. 238, col. 2, para 2.
Biosense Webster, Inc. (CA, USA) manufactures the LASSO 2515 Variable Circular Mapping Catheter, 2010.
Wustmann, "Effects of chronic baroreceptor stimulation on the autonomic cardiovascular regulation in patients with drug-resistant arterial hypertension", Hypertension 2009; 54;530-536.
Yao Sheng-Kun, "Endogenous and exogenous nitric oxide protect against intracoronary thrombosis and reclusion after thrombolysis" Circulation. 1995;92 pp. 1005-1010.
Heart rate variability, by Task Force of the European Society of Cardiology and the North American Society of Pacing and Electrophysiology, European Heart Journal (1996) 17, 354-381.
Vallais, "Heart rate and vasomotor control during exercise", Proceedings of the 29th Annual International Conference of the IEEE EMBS, Cité Internationale, Lyon, France, Aug. 23-26, 2007.
Sabbah H et al., "Global left ventricular remodeling with the Acorn Cardiac Support Device: Hemodynamic and angiographic findings in dogs with heart failure" Heart Failure Reviews 10(2):109-115 (2005) first page.
Kass D., Eur Heart J. Nov. 1992;13 Suppl. E:57-64.
Steendijk et al., European Heart Journal (2004) 6 (Supplement D), D35-D42.
Suga et al., Am J Physiol. Jan. 1981;240(1):H39-44.
Kong et al. "Tumour necrosis factor-α and its receptors in the beneficial effects of vagal stimulation after myocardial infarction in rats". Clin Exp Pharmacol Physiol. 2011;38:300-6.
Uemura et al., "Early short-term vagal nerve stimulation attenuates cardiac remodeling after reperfused myocardial infarction". J Card Fail. Aug. 2010;16(8):689-99.
Katare et al. "Vagal nerve stimulation prevents reperfusion injury through inhibition of opening of mitochondrial permeability transition pore independent of the bradycardiac effect". J Thorac Cardiovasc Surg. Jan. 2009;137(1):223-31.
Kawada et al. "Vagal stimulation suppresses ischemia-induced myocardial interstitial myoglobin release". Life Sci. Sep. 26, 2008;83(13-14):490-5.
Uemura et al. "Efferent vagal nerve stimulation induces tissue inhibitor of metalloproteinase-1 in myocardial ischemia-reperfusion injury in rabbit". Am J Physiol Heart Circ Physiol. Oct. 2007;293(4):H2254-61.
Mioni et al. "Activation of an efferent cholinergic pathway produces strong protection against myocardial ischemia/reperfusion injury in rats". Crit Care Med. Nov. 2005;33(11):2621-8.
An Office Action dated Jun. 19, 2012, which issued during the prosecution of U.S. Appl. No. 11/995,904.
An Office Action dated Aug. 29, 2012, which issued during the prosecution of U.S. Appl. No. 12/792,227.
U.S. Appl. No. 61/331,453, filed May 5, 2010.
An Office Action dated Aug. 1, 2012, which issued during the prosecution of U.S. Appl. No. 12/957,799.
An International Search Report and a Written Opinion both dated Jul. 5, 2012, which issued during the prosecution of Applicant's PCT/IL11/00952.
A Notice of Allowance dated Sep. 18, 2013, which issued during the prosecution of U.S. Appl. No. 13/210,778.
An Office Action dated Oct. 2, 2012, which issued during the prosecution of U.S. Appl. No. 12/851,214.
An Office Action dated Sep. 18, 2012, which issued during the prosecution of U.S. Appl. No. 12/023,896.
An English Translation of an Office Action dated Oct. 8, 2012, which issued during the prosecution of Chinese Patent Application No. 200980111617.8.
An Office Action dated Jul. 18, 2012, which issued during the prosecution of U.S. Appl. No. 13/210,778.
An Office Action dated Mar. 12, 2013, which issued during the prosecution of U.S. Appl. No. 13/210,778.
A Supplementary European search Report dated Dec. 14, 2012, which issued during the prosecution of European Patent Application No. 06766171.
An Office Action dated Apr. 25, 2013, which issued during the prosecution of U.S. Appl. No. 11/995,904.
An Office Action dated May 10, 2013, which issued during the prosecution of U.S. Appl. No. 12/023,896.
An Office Action dated Apr. 5, 2013, which issued during the prosecution of U.S. Appl. No. 12/792,227.
Takahata, "Stentenna: a Micromachined Antenna Stent for Wireless Monitoring of Implantable Microsensors" Engineering in Med. and Biol. Soci, 2003. Proceedings of the 25th Annual Intern Conference of the IEEE Sep. 17-21, 2003.
An Office Action dated Dec. 13, 2013, which issued during the prosecution of U.S. Appl. No. 13/294,062.
An Office Action dated Jan. 27, 2014, which issued during the prosecution of U.S. Appl. No. 12/023,896.
Extended European Search Report dated Oct. 31, 2013 which issued during the prosecution of Applicant's European App No. 11814203.3.
U.S. Appl. No. 61/532,660, filed Sep. 9, 2011.
An Office Action dated Nov. 12, 2013, which issued during the prosecution of U.S. Appl. No. 11/995,904.
An Office Action dated Dec. 20, 2013, which issued during the prosecution of U.S. Appl. No. 12/792,227.
Hennig et al. "Analysis of Power Absorption by Human Tissue in Deeply Implantable Medical Sensor Transponders" pp. 407-420, Advanced Microwave Circuits and Systems, Published online Apr. 1, 2010.
Gabriel et al. The dielectric properties of biological tissues: II. Measurements in the frequency range 10 Hz to 20 GHz, Phys. Med. Biol.41 (1996) 2251-2269.
An Office Action dated Aug. 7, 2019, which issued during the prosecution of U.S. Appl. No. 15/034,803.
An Office Action dated May 16, 2018, which issued during the prosecution of U.S. Appl. No. 15/034,803.
An Office Action dated Nov. 26, 2018, which issued during the prosecution of U.S. Appl. No. 15/034,803.
Notice of Allowance dated Feb. 12, 2020, which issued during the prosecution of U.S. Appl. No. 15/034,803.
Notice of Allowance dated Jul. 22, 2020, which issued during the prosecution of U.S. Appl. No. 15/354,313.
European Search Report dated Jun. 29, 2016 which issued during the prosecution of Applicant's European App No. 12830322.9.
An Office Action dated Jan. 5, 2015, which issued during the prosecution of U.S. Appl. No. 12/959,126.
An International Search Report and a Written Opinion both dated Aug. 8, 2013, which issued during the prosecution of Applicant's PCT/IL2013/050375.
An Office Action dated Jan. 15, 2015, which issued during the prosecution of U.S. Appl. No. 14/356,829.
An Office Action dated Dec. 4, 2017, which issued during the prosecution of U.S. Appl. No. 15/354,313.

(56) References Cited

OTHER PUBLICATIONS

An Office Action dated Feb. 11, 2019, which issued during the prosecution of U.S. Appl. No. 15/354,313.
An Office Action dated Nov. 27, 2019, which issued during the prosecution of U.S. Appl. No. 15/354,313.
An English translation of an Office Action dated May 6, 2020, which issued during the prosecution of Chinese Patent Application No. 201680022252.1.
An Interview Summary dated May 14, 2019, which issued during the prosecution of U.S. Appl. No. 15/354,313.
An English translation of an Office Action dated Sep. 2, 2019, which issued during the prosecution of Chinese Patent Application No. 201680022252.1.
"Stent", Free Online Medical Dictionary, pp. 1-3, accessed Jul. 17, 2013. (Year: 2013).
U.S. Appl. No. 61/183,319, filed Jun. 2, 2009.
An English Summary of an Office Action dated Dec. 26, 2019, which issued during the prosecution of Chinese Patent Application No. 201810648157.3.
An International Search Report and a Written Opinion both dated Apr. 16, 2015, which issued during the prosecution of Applicant's PCT/IL2014/050972.
An Office Action dated Jan. 4, 2016, which issued during the prosecution of U.S. Appl. No. 13/741,154.
An Office Action dated May 22, 2015, which issued during the prosecution of U.S. Appl. No. 13/741,154.
An Office Action dated Nov. 7, 2014, which issued during the prosecution of U.S. Appl. No. 13/741,154.
An Office Action dated May 18, 2018, which issued during the prosecution of U.S. Appl. No. 15/354,313.
An Office Action dated Sep. 12, 2018, which issued during the prosecution of U.S. Appl. No. 14/486,081.
An Office Action dated Aug. 5, 2019, which issued during the prosecution of European Patent Application No. 14859833.7.
An English Summary of an Office Action dated Mar. 7, 2019, which issued during the prosecution of Chinese Patent Application No. 201680022252.1.
An English Summary of an Office Action dated Jul. 16, 2020, which issued during the prosecution of Chinese Patent Application No. 201810648157.3.
U.S. Appl. No. 60/721,728, filed Sep. 28, 2005.
U.S. Appl. No. 60/702,491, filed Jul. 25, 2005.
PCT Notification of Transmittal Of The International Search Report and The Written Opinion Of The International Searching Authority, Or The Declaration For International Application No. PCT/IL14/50972 filed Nov. 6, 2014.
English translation of an Office Action dated Apr. 1, 2017 issued during the prosecution of Chinese Patent Application No. 201480072391.6.
Extended European Search Report dated Jun. 9, 2017 issued during the prosecution of European Patent Application No. 14859833.7.

\* cited by examiner

ANTENNA POSTS

CROSS-REFERENCES TO RELATED APPLICATIONS

The present application is a continuation of U.S. Ser. No. 15/034,803 to Dagan (published as US 2016/0278951), filed May 5, 2016, which is a US national phase application of PCT Application No. PCT/IL/2014/050972 to Dagan (published as WO 15/068167), entitled "Wireless endovascular stent-based electrodes," filed Nov. 6, 2014, which claims priority from U.S. Provisional Patent Application 61/900,461 to Dagan, entitled "Wireless endovascular stent-based electrodes," filed Nov. 6, 2013. Each of the above applications is incorporated herein by reference.

The present application is related to International application PCT/IL2013/050375 (published as WO 13/164829), filed May 2, 2013, entitled "Wireless endovascular stent-based electrodes," which claims priority from the following US provisional patent applications, which are incorporated herein by reference:

- U.S. Provisional Patent Application 61/641,388 to Dagan, filed May 2, 2012, entitled "Wireless endovascular stent-based electrodes;"
- U.S. Provisional Patent Application 61/714,277 to Dagan, filed Oct. 16, 2012, entitled, "Wireless endovascular stent-based electrodes;" and
- U.S. Provisional Patent Application 61/773,919 to Dagan, filed Mar. 7, 2013, entitled, "Wireless endovascular stent-based electrodes."

The present application is related to U.S. Ser. No. 13/741,154 to Dagan (issued as U.S. Pat. No. 9,526,637), which is the US national phase of International application PCT/IL2012/000336 (published as WO 13/035092), filed Sep. 9, 2012, entitled "Wireless endovascular stent-based electrodes," which claims priority from U.S. Provisional Patent Application 61/532,660 to Dagan, filed Sep. 9, 2011, entitled, "Wireless endovascular stent-based electrodes."

The present application is related to U.S. Ser. No. 13/210,778 to Dagan (issued as U.S. Pat. No. 8,626,290), filed Aug. 16, 2011, which is a continuation-in-part of U.S. Ser. No. 12/957,799 to Gross (issued as U.S. Pat. No. 8,626,299), filed Dec. 1, 2010, entitled "Thoracic aorta and vagus nerve stimulation," which is a continuation-in-part of U.S. Ser. No. 12/792,227 to Gross (published as US 2010/0305392, now abandoned), filed Jun. 2, 2010, entitled "Thoracic aorta and vagus nerve stimulation," which claims the benefit of (a) U.S. Provisional Patent Application 61/183,319 to Reisner, filed Jun. 2, 2009, entitled "Thoracic aorta and vagus nerve stimulation," and (b) U.S. Provisional Patent Application 61/331,453 to Dagan, filed May 5, 2010, entitled "Thoracic aorta and vagus nerve stimulation."

All of the above-referenced applications are incorporated herein by reference.

FIELD OF EMBODIMENTS OF THE INVENTION

Some applications of the present invention generally relate to medical apparatus. Specifically, some applications of the present invention relate to stent-based electrodes for placement in a blood vessel.

BACKGROUND

Heart failure is a condition in which a problem with the structure or function of the heart impairs its ability to supply sufficient blood flow to meet the body's needs. The condition impairs quality of life and is a leading cause of hospitalizations and mortality in the Western world. Treatment of heart failure is typically aimed at removal of precipitating causes, prevention of deterioration in cardiac function, and control of congestive state.

Hypertension, or chronic high blood pressure, is an extremely prevalent medical condition, which can lead to strokes, heart attacks, and heart failure. There are a variety of treatments that are available for treating hypertension, including lifestyle changes and medication.

SUMMARY OF EMBODIMENTS

In accordance with some applications of the present invention, a stent is placed within a lumen e.g., a lumen of a blood vessel of a subject, such as the subject's aorta. Typically, the stent defines a stent body, a plurality of antenna posts that protrude from a distal end of the stent body, a plurality of electrode posts that protrude from the distal end of the stent body, and one or more coupling elements for coupling a control capsule to the inner surface of the stent body. Further typically, an antenna is coupled to the stent by being sutured to the antenna posts that protrude from the stent body, a plurality of coiled electrodes are coupled to the stent by being placed upon respective electrode posts, and a control capsule is coupled to stent via the coupling elements. For some applications, a control unit and a transmitter are disposed outside the subject's body. The control unit transmits a signal and/or power toward the stent, via the transmitter. The antenna receives the transmitted signal and/or power, and the control capsule drives the electrodes to drive a current into the blood vessel, in response to the antenna receiving the signal and/or power.

For some applications, the stent includes a generally cylindrical stent body, which includes a generally cylindrical distal section, and a generally cylindrical middle section. The middle section of the stent body includes a plurality of strut rings that are flexibly interconnected to each other, by a plurality of bridges, such as to facilitate curving of the generally cylindrical middle section. The distal section of the stent body, from which the antenna posts protrude, includes at least one distal-section strut ring. The distal and middle sections of the stent body are configured such that, when the stent body is in a radially compressed configuration thereof (for example, when the stent body expands against the inner wall of the subject's blood vessel), the distal-section strut ring exerts an outward radial force that is greater than the outward radial force exerted by each of the middle-section strut rings.

For some applications, each of the antenna posts defines a proximal portion and a distal portion, each of which is configured to be generally straight in the absence of any force being applied to the antenna post. A compliant junction is disposed between the proximal portion and distal portion of the antenna post, and the proximal portion and distal portion are configured to flex with respect to one another about the compliant junction. For some applications, the compliant junction defines a single sinusoidal wave, 1.5 sinusoidal waves, or a different number of sinusoidal waves.

Typically the stent is placed inside the subject's aorta such that the distal end of the stent is in the vicinity of the subject's aortic arch. For some applications, the stent is placed such that the electrodes are disposed between the bifurcation of the aorta with the left subclavian artery and the bifurcation of the aorta with the fifth intercostal artery. For some applications, the control capsule drives the electrodes to drive a current into the subject's aorta, e.g., in order to treat the subject for a condition such as congestive heart failure, diastolic heart failure, and/or hypertension, e.g., as described in U.S. Ser. No. 13/210,778 to Dagan (published as US 2012/0035679), U.S. Ser. No. 12/957,799 to Gross (published as US 2011/0137370), and/or U.S. Ser. No. 12/792,227 to Gross (published as US 2010/0305392), all of which applications are incorporated herein by reference.

It is noted that in the context of the present application, the terms "proximal" and "distal" are to be understood to be with respect to an access point of the stent into the subject's body. Thus, the distal end of the stent is the end of the stent that is further from the access point, and the proximal end of the stent is the end of the stent that is closest to the access point. For applications in which the stent is placed inside the subject's aorta, the term "distal" typically means the portion of the stent or the aorta that is closer to the subject's left ventricle, and the term "proximal" means the portion of the stent or the aorta that is further from the subject's left ventricle.

There is therefore provided, in accordance with some applications of the present invention, apparatus for use with a tubular structure shaped to define a lumen thereof, the apparatus including:

a stent configured to be placed within the lumen, the stent including:

a generally cylindrical stent body, including a generally cylindrical distal section, and a generally cylindrical middle section, the middle section of the stent body including a plurality of middle-section strut rings, each of the plurality of middle-section strut rings including a plurality of middle-section struts, middle-section strut rings that are adjacent to one another being flexibly interconnected to one another, by a plurality of bridges, such as to facilitate curving of the generally cylindrical middle section, the distal section of the stent body including at least one distal-section strut ring, and the distal and middle sections of the stent body being configured such that, when the stent body is in a radially compressed configuration thereof, the at least one distal-section strut ring exerts an outward radial force that is greater than an outward radial force exerted by each of the middle-section strut rings; and a plurality of antenna posts protruding longitudinally from the distal section; and an antenna disposed annularly on the antenna posts.

For some applications:

the lumen of the tubular structure includes a lumen of a blood vessel of a subject, the stent is configured to be placed within the lumen of the blood vessel, and the distal and middle sections of the stent body are configured such that the at least one distal-section strut ring exerts a radial force on a wall of the blood vessel that is greater than a radial force exerted by each of the middle-section strut rings.

For some applications:

the lumen of the tubular structure includes a lumen of a blood vessel of a subject, the blood vessel including a curved portion shaped to define a curve, an inner wall of the blood vessel at the curved portion of the blood vessel defining an inner region that is on an inside of the curve and an outer region that is on an outside of the curve, the stent is configured to be placed within the lumen of the blood vessel at the curved portion of the blood vessel, and the middle-section strut rings that are adjacent to one another are flexibly interconnected to one another, such as to facilitate a longitudinal expansion of the stent body along the outer region of the inner wall of the blood vessel that is greater than a longitudinal expansion along the inner region of the inner wall of the blood vessel.

For some applications, the middle-section strut rings that are adjacent to one another are flexibly interconnected to one another, such as to facilitate a longitudinal expansion of the stent body along the outer region of the inner wall of the blood vessel, and a longitudinal compression of the stent body along the inner region of the inner wall of the blood vessel.

For some applications:

the at least one distal-section strut ring includes a plurality of thickened distal-section struts, each of the thickened distal-section struts having a greater cross-sectional area than each of a majority of the middle-section struts, and the at least one distal-section strut ring is configured to exert a greater outward radial force by virtue of including the thickened distal-section struts.

For some applications, each of a majority of the thickened distal-section struts is longer than each of a majority of the middle-section struts.

For some applications, the stent body further includes a generally cylindrical proximal section, the proximal section of the stent body including a proximal-section strut ring, the proximal and middle sections of the stent body being configured such that, when the stent body is in the radially compressed configuration thereof, the proximal-section strut ring exerts an outward radial force that is greater than an outward radial force exerted by each of the middle-section strut rings.

For some applications:

the proximal-section strut ring includes a plurality of thickened proximal-section struts, each of the thickened proximal-section struts having a greater cross-sectional area than each of a majority of the middle-section struts, and the proximal-section strut ring is configured to exert a greater outward radial force by virtue of including the thickened proximal-section struts.

For some applications, each of a majority of the thickened proximal-section struts is longer than each of a majority of the middle-section struts.

For some applications, the distal section of the stent body further includes a second distal-section strut ring, the second distal-section strut ring defining a plurality of distally-facing v-shaped strut pairs and the at least one distal-section strut ring defining a plurality of proximally-facing v-shaped strut pairs, and the second distal-section strut ring and the at least one distal-section strut ring are coupled to each other such that each distally-facing v-shaped strut pair of the second distal-section strut ring is coupled to one of the proximally-facing v-shaped strut pair of the at least one distal-section strut ring, such as to form a closed diamond-shaped cell.

For some applications, the apparatus further includes a plurality of electrodes;

the stent further includes a plurality of electrode posts coupled to the at least one distal-section strut ring, each of the electrodes being coupled to the stent by being placed on a respective electrode post, and the closed-cell arrangement of the distal section is configured to radially expand within the lumen of the tubular structure such that:

a proximal end of each of the electrodes is brought into contact with an inner wall of the tubular structure, and points of contact that the proximal ends of the electrodes make with the inner wall generally circumscribe a plane, a normal to the plane being generally parallel to a local longitudinal axis of the structure at the points of contact.

For some applications, the second distal-section strut ring is flexibly coupled to the at least one distal-section strut ring, such as to facilitate curving of the distal section of the stent body.

There is further provided, in accordance with some applications of the present invention, apparatus for use with a tubular structure shaped to define a lumen thereof, the apparatus including:

a stent configured to be placed in the lumen, the stent including:

a generally cylindrical stent body including a plurality of struts;

at least one electrode post protruding from the stent body; and a plurality of antenna posts protruding longitudinally from an end of the stent body, the antenna posts being longitudinally separated from the electrode post;

an antenna disposed annularly on the antenna posts, such that the antenna posts separate the antenna from the end of the stent body; and at least one electrode coupled to the stent by being placed on the electrode post.

For some applications, the lumen of the tubular structure includes a lumen of a blood vessel of a subject, and the stent is configured to be placed inside the lumen of subject's blood vessel.

For some applications, the lumen of the blood vessel includes a lumen of a curved portion of an aorta of the subject, and the stent is configured to be placed inside the lumen of the curved portion of the subject's aorta.

For some applications, the at least one electrode is a coiled electrode.

For some applications, the stent defines one or more coupling elements, the apparatus further including a control capsule that is configured to:

be coupled to the stent via the coupling elements, receive electrical power from the antenna; and drive a current through the electrodes, using the received electrical power.

For some applications:

the at least one electrode post includes a plurality of electrode posts;

the at least one electrode includes a plurality of electrode that are configured to be coupled to the stent by being placed on respective electrode posts of the plurality of electrode posts; and the plurality of electrode posts are disposed around less than 75 percent of a circumference of the stent.

For some applications, the plurality of electrode posts are disposed around less than 50 percent of the circumference of the stent.

For some applications, the plurality of electrode posts are disposed around less than 30 percent of the circumference of the stent.

For some applications, the stent defines one or more coupling elements, the apparatus further including a control capsule that is configured to:

be coupled to the stent via the coupling elements, receive electrical power from the antenna; and drive a current through the electrodes, using the received electrical power.

For some applications, the plurality of electrode posts and the coupling elements are disposed around less than 75 percent of the circumference of the stent, and the coupling elements are rotationally displaced with respect to all of the electrode posts defined by the stent.

For some applications, the plurality of electrode posts and the coupling elements are disposed around less than 50 percent of the circumference of the stent.

There is additionally provided, in accordance with some applications of the present invention a method including:

inserting into a curved portion of an aorta of a subject a self-expandable stent having a plurality of electrodes, an antenna, and a control capsule coupled thereto; and causing the stent to become anchored to an inner wall of the subject's aorta, such that all of the electrodes and the control capsule are disposed around less than 75 percent of a circumference of the aorta.

For some applications, causing the stent to become anchored to the inner wall of the subject's aorta, includes causing the stent to become anchored to the inner wall of the aorta such that all of the electrodes and the control capsule are disposed around less than 50 percent of a circumference of the aorta.

For some applications, the method further includes causing the control capsule to receive electrical power from the antenna, and to use the power to drive a current into the aorta via the electrodes, by operating a control unit to transmit RF power to the antenna.

For some applications, causing the stent to become anchored to the inner wall of the subject's aorta includes causing the stent to become anchored to the inner wall of the subject's aorta, such that the control capsule is rotationally displaced with respect to all of the electrodes.

For some applications, causing the stent to become anchored to the inner wall of the subject's aorta includes causing the stent to become anchored to the inner wall of the subject's aorta such that the control capsule is disposed along an outer region of the curved portion of the aorta, at which a curvature of the curved portion of the aorta is less than a curvature of an inner region of the curved portion of the aorta.

There is additionally provided, in accordance with some applications of the present invention, apparatus for use with a tubular structure shaped to define a lumen thereof, the apparatus including:

a stent configured to be placed in the lumen, the stent including:

a generally cylindrical stent body including a plurality of struts; and a plurality of antenna posts protruding longitudinally from an end of the stent body, each of the antenna posts including:

a proximal portion and a distal portion, each of which is configured to be generally straight in the absence of any force being applied to the antenna post; and a compliant junction disposed between the proximal portion and distal portion of the antenna post, the proximal portion and distal portion being configured to flex with respect to one another about the compliant junction; and an antenna disposed annularly on the distal portions of the antenna posts, such that the antenna posts separate the antenna from the end of the stent body.

For some applications, the lumen of the tubular structure includes a lumen of a blood vessel of a subject, and the stent is configured to be placed inside the lumen of subject's blood vessel.

For some applications, the compliant junction is shaped to define a single sinusoidal wave.

For some applications, the compliant junction is shaped to define 1.5 sinusoidal waves.

For some applications, the compliant junction is shaped to define 2 or more sinusoidal waves.

For some applications, the lumen of the blood vessel includes a lumen of a curved portion of an aorta of the subject, and the stent is configured to be placed inside the lumen of the curved portion of the subject's aorta.

For some applications, the compliant junction is configured to facilitate flexing of the distal portion of the antenna post with respect to the proximal portion of the antenna post, such that the post at least partially conforms with a curvature of the curved portion of the aorta even at an inner region of the curved portion of the aorta, at which a curvature of the curved portion of the aorta is greater than a curvature of an outer region of the curved portion of the aorta.

For some applications, the apparatus further includes a self-expandable wire that is coupled to the antenna, and that is configured self-expand inside the curved portion of the subject's aorta such as to bring the antenna into contact with an inner wall of the aorta, and the compliant junction is configured to facilitate flexing of the distal portion of the antenna post with respect to the proximal portion of the antenna post, such that the antenna is brought into contact with the inner wall of the aorta even at the inner region of the curved portion of the aorta.

There is further provided, in accordance with some applications of the present invention, apparatus for use with a blood vessel, the apparatus including:

a stent configured to be placed within the blood vessel, the stent including:
a generally cylindrical stent body including a plurality of undulating strut rings,
a distal-most undulating strut ring including N distal-most-ring strut pairs, and
a second undulating strut ring being adjacent to the distal-most undulating strut ring, the second undulating strut ring including N/2 second-ring strut pairs;
a plurality of antenna posts protruding longitudinally from the distal-most undulating strut ring; and
a plurality of electrode posts protruding from the distal-most undulating strut ring; and
an antenna disposed annularly on the antenna posts.

For some applications:
each of the distal-most-ring strut pairs includes two struts coupled at a respective proximal junction of the distal-most undulating strut ring,
adjacent distal-most-ring strut pairs are coupled to one another at respective distal junctions of the distal-most undulating strut ring,
each strut of each second-ring strut pair is coupled to a respective proximal junction of the distal-most undulating strut ring, such as to define N/2 closed-cell arrangements,
the plurality of antenna posts protrude longitudinally from respective distal junctions of the distal-most undulating strut ring, and
the plurality of electrode posts protrude from respective proximal junctions of the distal-most undulating strut ring.

For some applications, the apparatus further includes a plurality of electrodes, each electrode being coupled to the stent by being placed on one of the electrode posts.

For some applications, each of the electrode posts protrudes from a respective one of a plurality of consecutive proximal junctions.

For some applications:
a number of antenna posts is N/2, and
each of the antenna posts protrudes from a respective distal junction such that alternate distal junctions are coupled to an antenna post.

For some applications, N is an even integer between 9 and 15.

For some applications, N is 12.

The present invention will be more fully understood from the following detailed description of embodiments thereof, taken together with the drawings, in which:

DETAILED DESCRIPTION OF EMBODIMENTS

Figure 1:
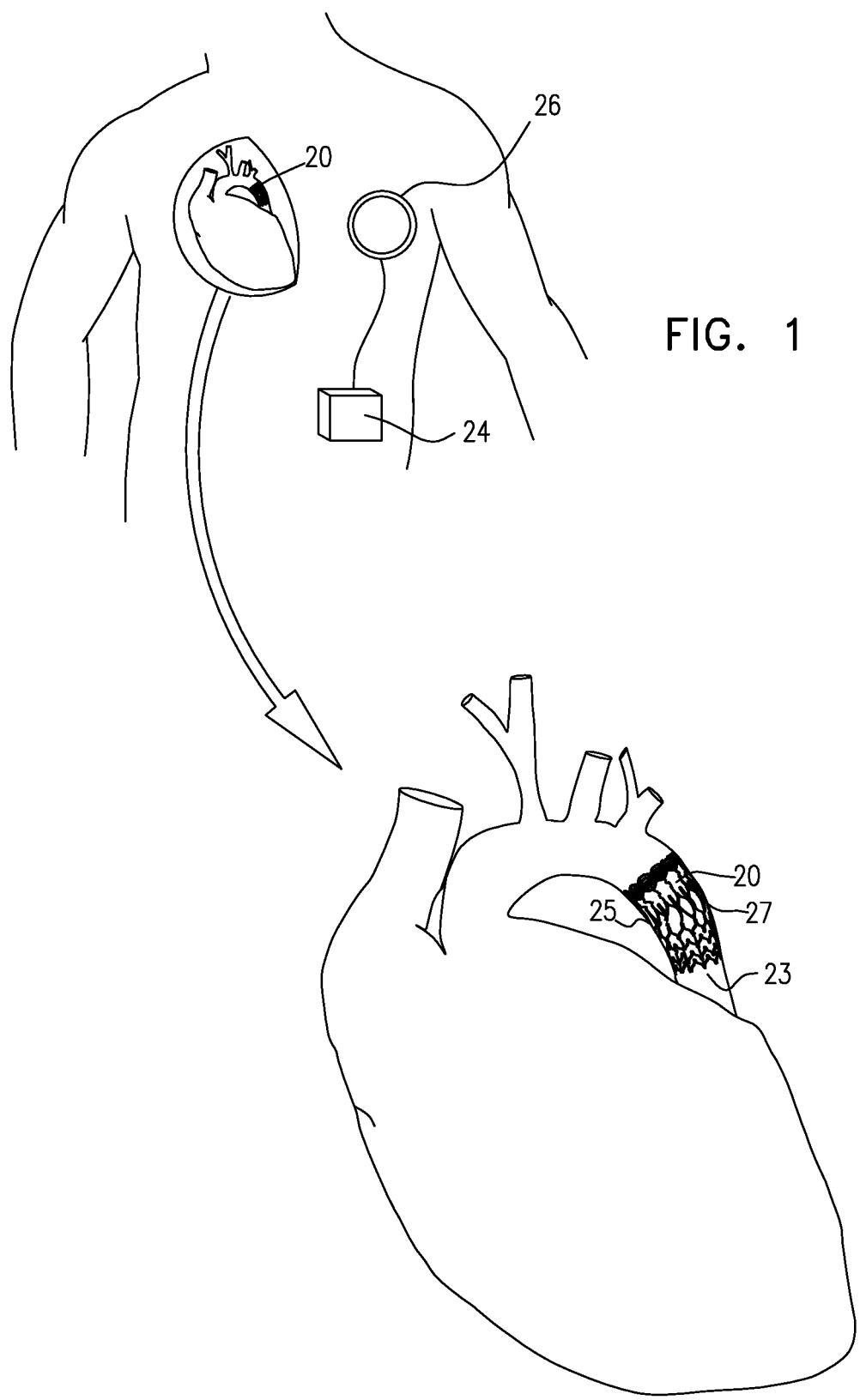
FIG. 1 is a schematic illustration of a stent having electrodes and an antenna disposed thereon, the stent having been placed inside a subject's aorta, in accordance with some applications of the present invention.
Figure 2A:
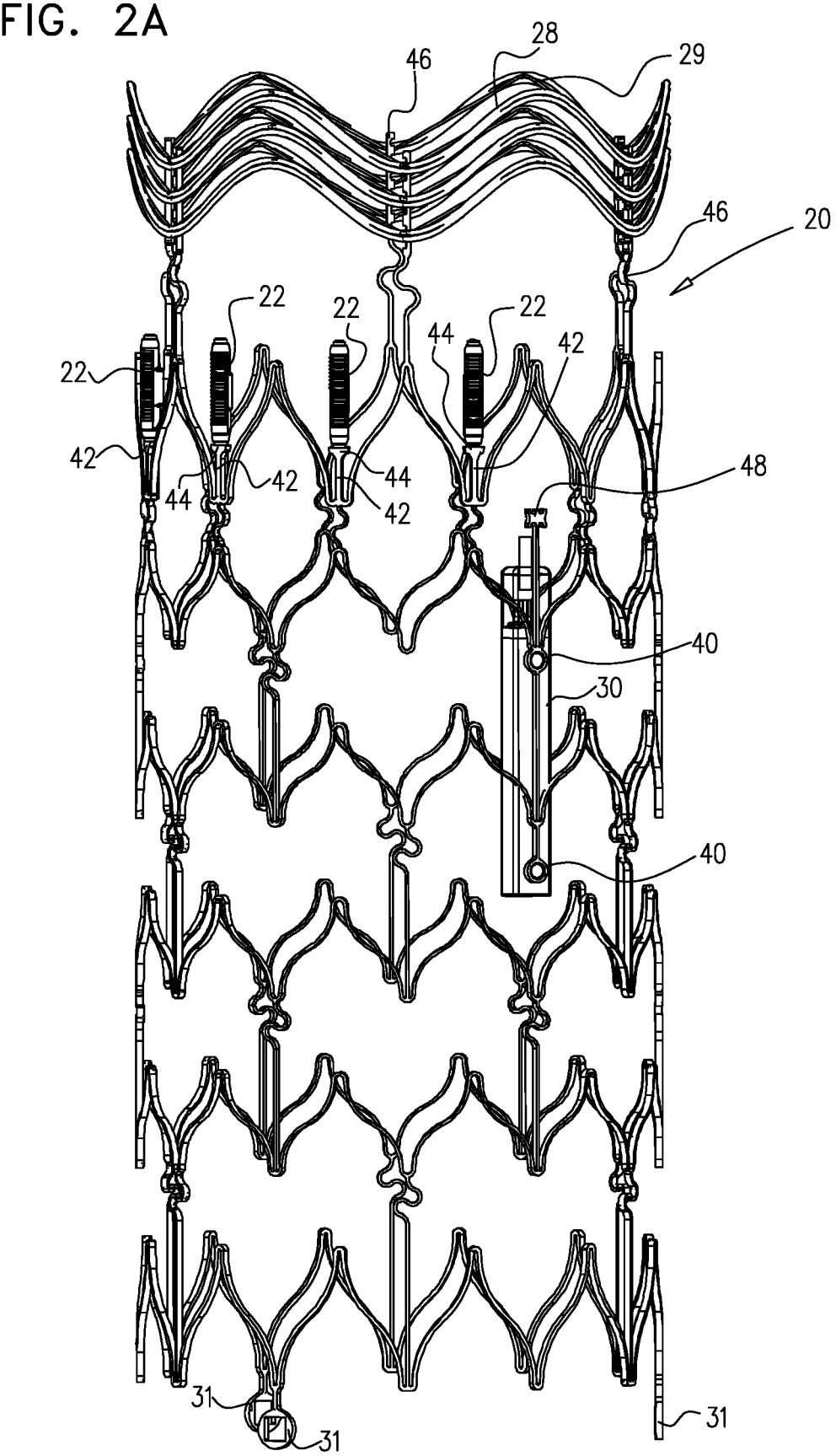
FIGS. 2A-B are schematic three-dimensional illustrations showing respective views of a self-expandable stent in its expanded configuration, in accordance with some applications of the present invention.
Figure 2B:
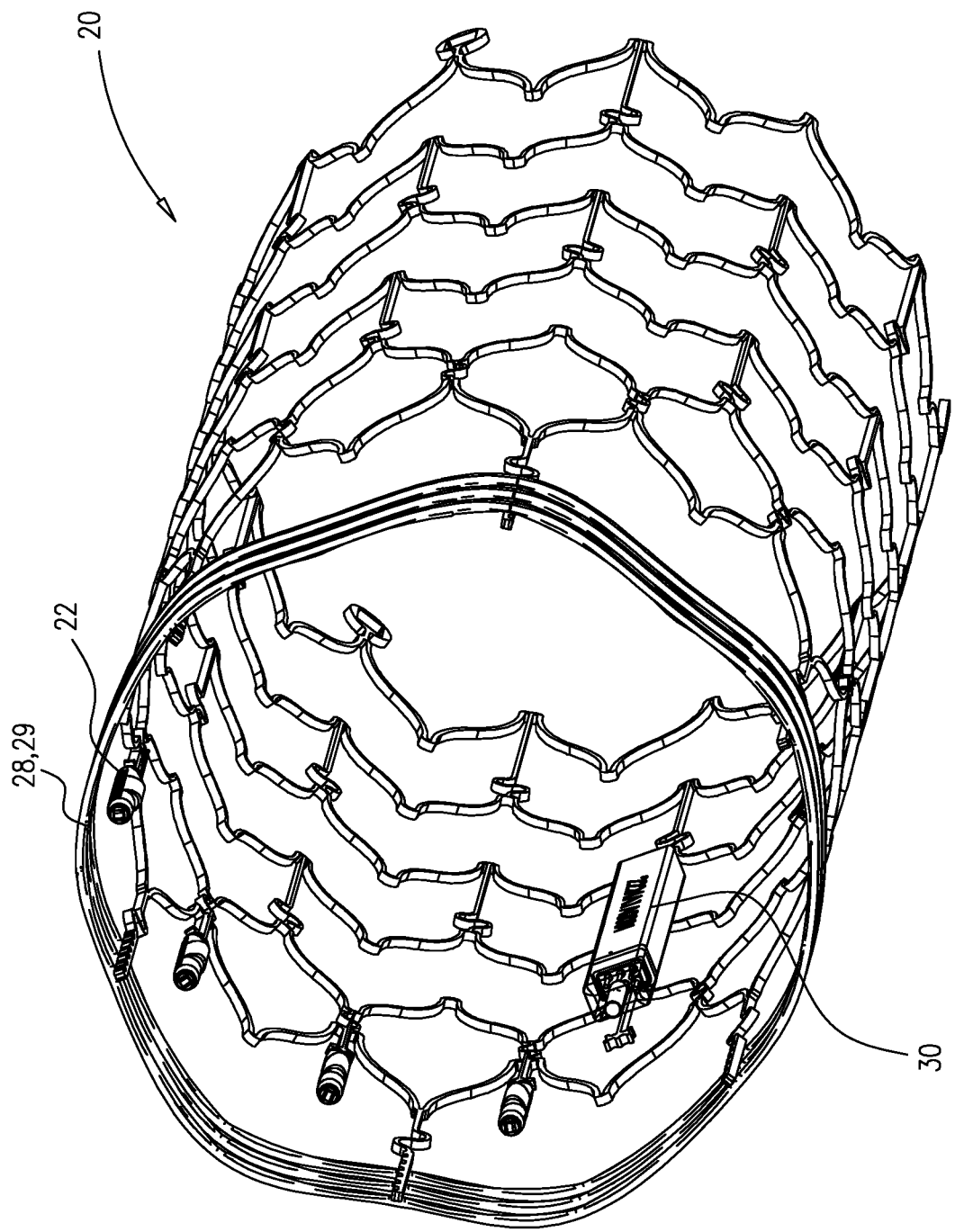

Reference is now made to FIG. 1, which is a schematic illustration of a self-expandable stent 20 placed inside a tubular structure, at least one electrode 22 (FIGS. 2A-B), and typically, a plurality of electrodes, being disposed on the stent, in accordance with some applications of the present invention. For some applications, stent 20 is placed inside a subject's blood vessel, stent 20 typically being placed inside the subject's aorta 23, as shown. Reference is also made to FIGS. 2A-B, which are schematic illustrations of the stent in its expanded configuration, and in the absence of the subject's anatomy, in accordance with some applications of the present invention. It is noted that the stent as depicted in FIG. 1 is illustrative, and that the appearance of the stent is typically as shown and described with reference to FIGS. 2A-B, and FIGS. 3-5.

Typically, a control unit 24 and a transmitter 26 are disposed outside the subject's body, as shown in FIG. 1. For some applications (not shown), the control unit and/or the transmitter are implanted (e.g., subcutaneously implanted) inside the subject's body. Typically, an antenna 28 and a control capsule 30 (FIGS. 2A-B) are coupled to stent 20. Control unit 24 transmits a signal and/or power toward stent 20, via transmitter 26. Antenna 28 receives the transmitted signal and/or power, and control capsule 30 drives the electrodes to drive a current into the blood vessel, in response to the antenna receiving the signal. For some applications, control capsule 30 transmits data to control unit 24 by transmitting a signal from antenna 28 toward transmitter 26. Thus, for some applications, antenna 28 may also act as a transmitter, and transmitter 26 may also act as a receiver. Typically, transmitter 26 and antenna 28 communicate with one another via inductive coupling. For some applications, control unit 24 is programmable using a computer. For example, a user (such as a physician) may use a computer (not shown) to program control unit 24, using a standard communication protocol, such as Bluetooth®, to facilitate communication between the computer and control unit 24.

Typically, electrodes 22 are placed in contact with an aortic site, which is as described in U.S. Ser. No. 13/210,778 to Dagan (issued as U.S. Pat. No. 8,626,290), U.S. Ser. No. 12/957,799 to Gross (issued as U.S. Pat. No. 8,626,299), and/or U.S. Ser. No. 12/792,227 to Gross (published as US 2010/0305392), all of which applications are incorporated herein by reference. The aortic site is typically between the bifurcation of the aorta with the left subclavian artery and the bifurcation of the aorta with the fifth intercostal artery. Further typically, the aortic site is between the bifurcation of the aorta with the left subclavian artery and the bifurcation of the aorta with the fourth intercostal artery, e.g., between the bifurcation of the aorta with the left subclavian artery and the bifurcation of the aorta with the first intercostal artery. For some applications, the aortic site is between the bifurcations of the aorta with the first and fifth intercostal arteries.

Typically, a current is driven into the subject's aorta, e.g., in order to treat the subject for a condition such as congestive heart failure, diastolic heart failure, and/or hypertension, e.g., as described in U.S. Ser. No. 13/210,778 to Dagan (issued as U.S. Pat. No. 8,626,290), U.S. Ser. No. 12/957,799 to Gross (issued as U.S. Pat. No. 8,626,299), and/or U.S. Ser. No. 12/792,227 to Gross (published as US 2010/0305392), all of which applications are incorporated herein by reference. For some applications, stent 20 is cut from a nitinol tube (or a tube made from a different material, such as stainless steel) having a wall thickness of more than 0.2 mm (e.g., more than 0.4 mm), and/or less than 0.7 mm (e.g., less than 0.6 mm). For some applications, the length of the stent is more than 25 mm (e.g., more than 30 mm), and/or less than 100 mm (e.g., less than 40 mm). The stent is shape set to a desired expanded configuration of the stent, using techniques that are known in the art. For some applications, the stent is shape set such that in its expanded configuration (i.e., in the absence of any forces acting on the stent), the stent has a maximum outer diameter of more than 10 mm (e.g., more than 15 mm), and/or less than 60 mm (e.g., less than 50 mm). The stent is typically configured such that, upon being deployed in its expanded configuration inside the subject's aorta, the stent anchors itself within the aorta by at least the ends of the stent body (and, typically, the entire stent body) expanding such as to contact the inner wall of the aorta. Furthermore, the stent is typically configured such that, upon being deployed in its expanded configuration inside the subject's aorta, the stent maintains electrodes 22 in contact with the aortic site, and the stent maintains antenna 28 in an open configuration, as described in further detail hereinbelow.

Stent 20 is typically configured to be placed inside the blood vessel (e.g., the aorta) percutaneously (e.g., transfemorally) using a delivery system, e.g., using a 12 Fr-20 Fr catheter (e.g., a 16 Fr catheter). In order to facilitate the percutaneous placement of the stent into the blood vessel (e.g., the aorta), using the catheter, the stent is crimped. Typically, the stent has a crimped profile of less than 20 Fr (e.g., 18 Fr or less), and/or more than 8 Fr (e.g., 10 Fr or more). Typically, stent 20 defines coupling elements 31 at a proximal end of the stent. For some applications, the coupling elements are disposed at a location along the length of the stent other than the proximal end of the stent. During insertion of the stent via the catheter, the delivery system holds the stent in place with respect to the catheter using the coupling elements. In order to place the stent inside the blood vessel at a deployment location, the catheter is retracted at the deployment location, such that the stent is released from the catheter. The stent becomes anchored to the blood vessel via radial expansion of the stent against the inner wall of the blood vessel. Subsequently, the coupling elements are decoupled from the delivery system, and the catheter is withdrawn from the blood vessel.

For some applications, upon being placed inside the blood vessel, the stent is partially deployed by retracting the catheter with respect to the stent, such that (a) electrodes 22 contact the wall of the blood vessel at a given location within the blood vessel, and (b) a proximal portion of the stent is disposed inside the catheter, such that the stent may be retrieved into the catheter. For some applications, the response of the subject to electrical stimulation of the blood vessel at the current location of the electrodes within the blood vessel is determined. In response thereto, the stent is (a) fully deployed at the current location of the stent, (b) retrieved into the catheter and redeployed at a different location within the blood vessel, or (c) retrieved into the catheter and removed from the subject's body (e.g., if the subject does not respond in a suitable manner to electrical stimulation of the blood vessel at any location at which the stent is deployed). Alternatively or additionally, prior to stent 20 being placed inside the blood vessel (e.g., inside the aorta), a mapping device is placed inside the blood vessel, the mapping device including stimulation electrodes. The subject's blood vessel is electrically stimulated at a plurality of stimulation sites using the stimulation electrodes of the mapping device, and the subject's response to electrical simulation at respective sites within the blood vessel is monitored. Subsequently, the mapping device is retrieved from the blood vessel, and stent 20 is placed inside the blood vessel. The location at which to deploy stent 20 within the blood vessel is determined, in response to the monitoring of the subject's responses to the stimulation at the respective sites using the mapping device.

Typically, the compliance of stent 20 is such that pulsation of the blood vessel is substantially maintained upon the stent being deployed inside the blood vessel. Further typically, the stent and components coupled thereto (such as control capsule 30) are shaped such as to substantially maintain blood flow through the blood vessel upon deployment of the stent inside the blood vessel.

As shown in FIG. 2A, stent 20 typically defines one or more coupling elements 40 for facilitating coupling of control capsule 30 to the stent. For some applications, as shown, the stent defines rings that define holes. The control capsule is coupled to the stent by inserting protrusions that protrude from the back of the control capsule into the rings. As shown, the control capsule is typically configured to be coupled to the stent such that the control capsule is disposed on the inner surface of the stent. For some applications, a length of the control capsule is more than 10 mm, less than 30 mm (e.g., less than 25 mm), and/or 10-30 mm (e.g., 10-25 mm). Typically, the width and depth of the capsule are each greater than 1 mm (e.g., greater than 2 mm), less than 5 mm (e.g., less than 3 mm), and/or 1-5 mm (e.g., 2-3 mm).

Typically, at least one electrode 22 is configured to be coupled to stent 20. For some applications, electrode 22 is coiled and is coupled to stent 20 by being placed upon an electrode post 42 that protrudes from the body of stent 20. The electrode is typically disposed on an electrode construction that is configured such that, when the electrode construction is placed on the electrode post, electrode 22 is electrically isolated from the antenna and from the stent body, for example as described with reference to FIGS. 8A-B of US 2014/0180391 to Dagan, which is incorporated herein by reference. For some applications, electrode post 42 is shaped to define protrusions 44, such as to prevent the electrode construction from sliding toward the stent body, when the electrode construction is coupled to the electrode post. Typically, at least 2 electrodes (e.g., at least 3 electrodes), and/or less than 12 electrodes (e.g., less than 6 electrodes) are coupled to stent 20, respective electrodes being placed upon respective electrode posts that protrude from the stent body. For example, 3-5 electrodes (e.g., 4 electrodes) may be coupled to stent 20, respective electrodes being placed upon respective electrode posts that protrude from the stent body.

Typically, antenna 28 is made of a metal wire, e.g., a gold wire. In order for transmitter 26 to communicate with antenna 28 via inductive coupling, it is typically desirable that the antenna become fully expanded inside the blood vessel, such that the antenna is in contact with the inner wall of the blood vessel. For some applications, in order to facilitate expansion of the antenna inside the subject's blood vessel, nitinol wire 29 is coupled to the gold wire, and the nitinol wire is shape set in a desired expanded configuration of the antenna. The distal end of the delivery catheter that is used to deliver stent 20 is retracted at the deployment location of the stent, as described hereinabove. The retraction of the delivery catheter causes the nitinol wire to self-expand inside the subject's blood vessel, and due to the coupling of the nitinol wire to the gold wire, the nitinol wire causes the antenna to expand into the desired expanded configuration (e.g., such that the antenna is in contact with the inner wall of the blood vessel). Typically, the antenna includes a plurality of turns of the gold wire. For example, the antenna may include more than 2 turns, and/or less than 12 turns, e.g. 2-12 turns or 2-6 turns. For some applications, the antenna includes 6 turns of the gold wire, the six turns of wire being separated into 3 levels that are separated from another, as shown. For some applications, the antenna wires are shaped in a waved configuration, as shown.

Antenna 28 and nitinol wire 29 are typically coupled to stent 20 by being sutured to antenna posts 46, which protrude from the stent body of stent 20 separately from electrode posts 42. As described hereinabove, for some applications, antenna 28 is used to receive electrical power for powering the control capsule 30 to drive a current via electrodes 22. Typically, the antenna receives power via inductive coupling, e.g., by transmitter 26 (shown in FIG. 1), or a different transmitter, transmitting RF energy toward antenna 28, such as to generate a magnetic field through the antenna. The magnetic field passing through antenna 28 generates an inductive current through antenna 28. The current through antenna 28 in turn generates a magnetic field, which can generate an inductive current through the body of stent 20, which may interfere with the antenna current, and reduce the efficiency of the electrical powering of the control capsule. The antenna posts are configured such that, when the antenna is sutured to the antenna posts, the antenna is separated from the distal end of the stent body. For some applications, by separating the antenna from the distal end of the stent body, the posts reduce the strength of the inductive current that is generated in the stent body, thereby increasing the efficiency of the electrical powering of the control capsule, via the inductive current that is generated through the antenna. For some applications, a length L (FIG. 3) of each of antenna posts 46 is less than 20 mm, e.g., less than 15 mm, and/or greater than 1 mm, e.g., greater than 5 mm.

As described hereinabove, stent 20 defines electrode posts 42, which are separate from antenna posts 46. The electrode posts and the antenna posts are configured such as to provide a longitudinal separation between the electrodes and the antenna. In this manner, electrical interference between the antenna and the electrodes is reduced relative to if, for example, the electrodes were to be placed upon the antenna posts.

Typically, antenna 28 is wiredly coupled to control capsule 30 (wires not shown), and the control capsule is powered using the inductive current of the antenna. For some applications, the inductive current of the antenna is the only source of power for the control capsule. The control capsule is typically configured to drive a current into the blood vessel via electrode 22 (e.g., to stimulate the blood vessel), and/or to receive an electrical parameter of the blood vessel via the electrode. Typically, the control capsule is wiredly coupled to electrode 22 (wires not shown), and, in cases in which there is more than one electrode 22, the control capsule is wiredly coupled to each of electrodes 22. For some applications, stent 20 is shaped to define a wire holder 48 that is configured to hold in place, with respect to the stent body, the wires that couple the antenna and the electrode(s) to the control capsule, by the wires being threaded through slots defined by the wire holder.

As described hereinabove, typically at least 2 electrodes 22 (e.g., at least 3 electrodes), and/or less than 12 electrodes (e.g., less than 6 electrodes) are coupled to stent 20, respective electrodes being placed upon respective electrode posts that protrude from the stent body. For example, 3-5 electrodes (e.g., 4 electrodes) are coupled to stent 20, respective electrodes being placed upon respective electrode posts that protrude from the stent body. For some applications, electrodes 22 are disposed evenly around the circumference of stent 20. Typically, as shown in FIGS. 2A-B, electrodes 22 are not disposed evenly around the circumference of stent 20. As shown in FIG. 1, stent 20 is typically placed inside the subject's aorta, in a curved portion of the aorta that is in the vicinity of the aortic arch. The curved portion defines an inner region 25 of the curve at which the curvature of the curved portion is greater, and an outer region 27 of the curve at which the curvature of the curved portion is lower. In experiments conducted by inventors of the present application, stimulation of the aorta was applied to 12 human subjects at aortic sites, as described hereinabove. The stimulation was applied at respective circumferential locations of the aorta at the aortic site, and the subjects' responses were measured. If one's perspective is looking along the descending aorta from the bottom of the ascending aorta toward the aortic arch, and the center of the outer region of the curved portion (i.e., the location at which the curvature of the curved portion of the aorta is at a minimum) is designated the 12 o'clock position, it was determined that the subjects typically responded best to stimulation at the aortic site at circumferential locations between the 7 o'clock and 12 o'clock positions.

Therefore, typically, 3-5 electrodes (e.g., 4 electrodes) are coupled to stent 20 such that when the stent is placed inside the subject's aorta, the electrodes are placed in contact with the aorta at an aortic site as described hereinabove, and at circumferential locations that are between the 5 o'clock and the 1 o'clock positions (e.g., between the 7 o'clock and 12 o'clock positions). For some applications, stent 20 defines 3-5 electrode posts 42 (e.g., 4 electrode posts), the electrode posts being disposed around less than 75 percent, e.g., less than 50 percent, or less than 30 percent of the circumference of stent 20, such that the electrodes are brought into contact with a corresponding portion of the circumference of the aorta. In this manner, using a given amount of power, the efficiency of driving the current into the aortic site, in terms of having a desired effect on the subject, is greater than if the current were to be applied evenly around the full circumference of the aorta at the aortic site.

In embodiments in which stent 20 is placed within a curved portion of the aorta, it is typically desirable that the control capsule (which has a flat surface) be placed toward the outside of the curve, where the curvature of the inner wall of the aorta is lower than that of the inner wall of the aorta toward the inside of the curve. Therefore, the one or more coupling elements 40, to which the control capsule is coupled, are typically disposed such that when the stent is deployed inside the aorta, the coupling elements (and therefore, the control capsule) are disposed between the 9 o'clock and 3 o'clock positions (e.g., between the 10 o'clock and 2 o'clock positions), and the electrode posts and the electrodes are disposed between the 5 o'clock and the 1 o'clock positions (e.g., between the 7 o'clock and 12 o'clock positions). Further typically, all of the electrode posts, as well as the one or more coupling elements 40 (and therefore, the control capsule) are disposed around less than 75 percent of the circumference of the stent, e.g., around less than 50 percent of the circumference of the stent. In addition, when looking along the stent from the proximal end of the stent (i.e., the opposite end of the stent from the end from which the antenna posts protrude) to the distal end of the stent (i.e., the end of the stent from the end from which the antenna posts protrude), the one or more coupling elements 40 (and therefore, the control capsule) are disposed at a clockwise rotational displacement (e.g., a clockwise rotational displacement of less than 30 degrees) from all of the electrode posts, as shown.

For some applications (not shown), electrode posts 42 are evenly spaced around the full circumference of the distal end of stent 20, as described hereinabove.

Figure 3:
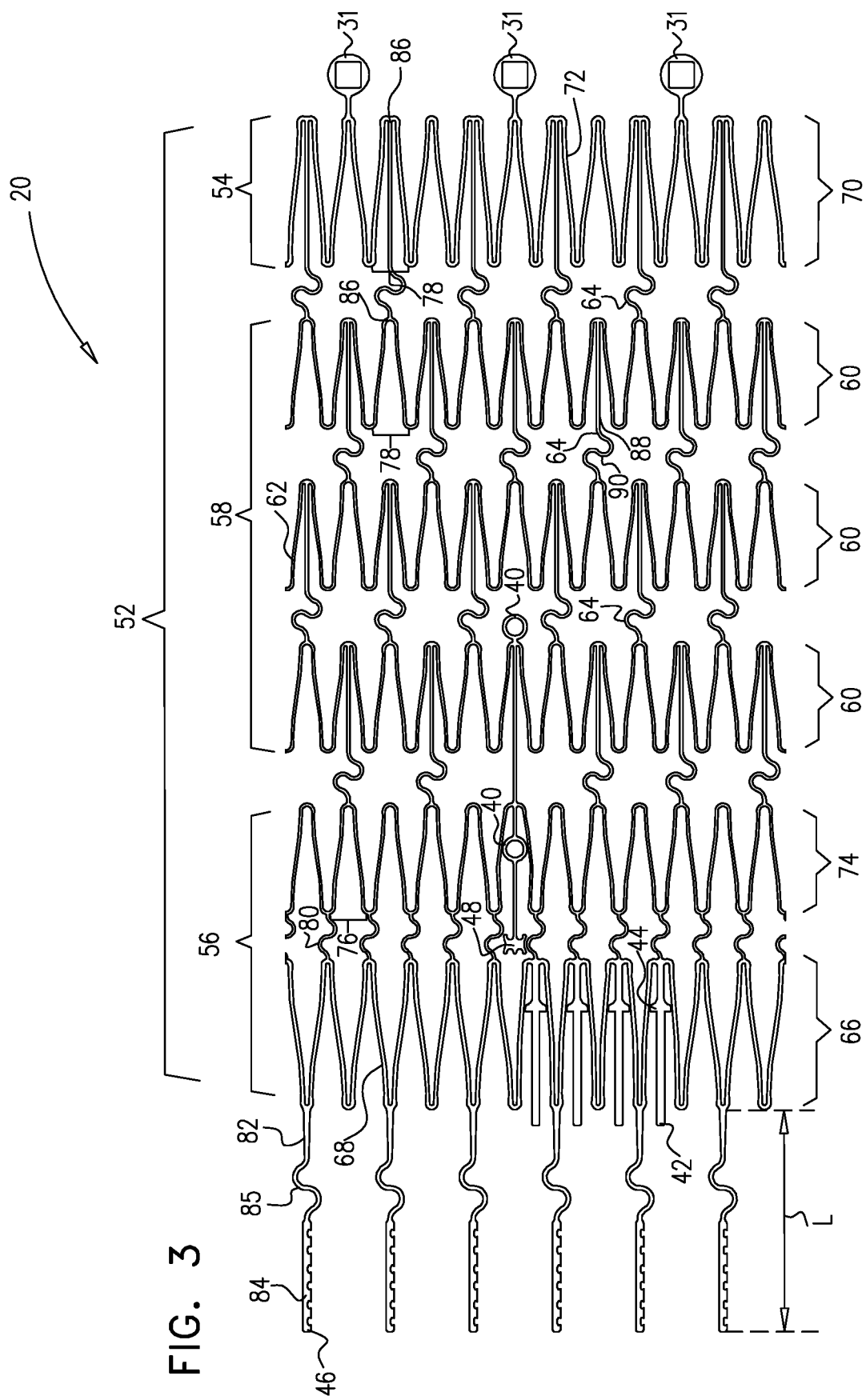
FIG. 3 is a schematic illustration showing the structure of a stent for placing inside a blood vessel, in accordance with some applications of the present invention.

Reference is now made to FIG. 3, which is a schematic illustration of stent 20, in accordance with some applications of the present invention. FIG. 3 shows a flattened profile of the stent, which depicts (for illustrative purposes) how the stent would appear if a longitudinal incision were to be made along the length of the stent at a given circumferential location of the stent, and the stent were to then be laid out flat upon a surface. Stent 20, as shown in FIG. 3, comprises a generally cylindrical stent body 52 comprising a generally cylindrical proximal section 54, a generally cylindrical distal section 56, and a generally cylindrical middle section 58. In the context of the present application, the term "section" should be understood as referring to a cylindrical portion of stent 20. As further described hereinbelow, a "section" typically comprises one or more strut rings, i.e., ring-shaped formations of struts, along with other elements, e.g., coupling elements such as bridges or flexible junctions.

Middle section 58 comprises a plurality of middle-section strut rings 60, each middle-section strut ring 60 comprising a plurality of middle-section struts 62. Middle-section strut rings 60 that are adjacent to one another are flexibly interconnected to one another by a plurality of bridges 64. The flexible interconnection of adjacent rings 60 facilitates curving of middle section 58, which in turn facilitates placement of the middle section within a curved portion of the blood vessel, e.g., at an aortic site in the vicinity of a subject's aortic arch, as described herein.

Distal section 56 comprises at least one distal-section strut ring 66. Distal section 56 and middle section 58 are configured such that, when stent body 52 is in a radially compressed configuration thereof, distal-section strut ring 66 exerts an outward radial force that is greater than an outward radial force exerted by each of the middle-section strut rings 60. For example, when placed within a blood vessel, the wall of the blood vessel radially compresses stent body 52, and distal-section strut ring 66 exerts a radial force on the wall that is greater than the radial force exerted by each of middle-section strut rings 60. The greater radial force exerted by distal-section strut ring 66 helps distal section 56 anchor stent 20 in place, i.e., it helps distal section 56 generally remain in place at a desired position within the blood vessel. Furthermore, the greater radial force exerted by distal-section strut ring 66 helps distal section 56 maintain electrodes 22 in contact with the inner wall of the blood vessel, and maintain antenna 28 in an open configuration.

For some applications, as shown in FIG. 3, distal-section strut ring 66 comprises a plurality of thickened distal-section struts 68, each thickened strut 68 having a greater cross-sectional area than each of a majority of middle-section struts 62. (In the example shown in FIG. 3, each thickened strut 68 has a greater cross-sectional area than each of middle-section struts 62.) In such applications, distal-section strut ring 66 is configured to exert a greater outward radial force by virtue of distal-section struts 68 being thickened. For some applications, also as shown in FIG. 3, each of a majority of thickened distal-section struts 68 is longer than each of a majority of middle-section struts 62. (In the example shown in FIG. 3, each thickened strut 68 is longer than each of middle-section struts 62.) Typically, the increased length of thickened struts 68 helps reduce strain on distal section 56 that may result from the increased cross-sectional area of thickened struts 68.

Stent 20 further comprises a plurality of antenna posts 46 protruding longitudinally from distal section 56, the antenna posts being generally as described hereinabove. The apparatus typically includes antenna 28 (not shown in FIG. 3) disposed annularly on antenna posts 46, the antenna typically being made of gold and being supported by nitinol wire 29, as described hereinabove.

With reference again made to FIG. 1, stent 20 is configured to be placed within a curved portion of a blood vessel. For example, for some applications, stent 20 is configured to be placed inside the subject's aorta, at an aortic site in the vicinity of the subject's aortic arch. The aortic site is typically between the bifurcation of the aorta with the left subclavian artery and the bifurcation of the aorta with the fifth intercostal artery. Further typically, the aortic site is between the bifurcation of the aorta with the left subclavian artery and the bifurcation of the aorta with the fourth intercostal artery, e.g., between the bifurcation of the aorta with the left subclavian artery and the bifurcation of the aorta with the first intercostal artery. For some applications, the aortic site is between the bifurcations of the aorta with the first and fifth intercostal arteries.

As described hereinabove, the inner wall of the aorta at the aortic site defines an inner region 25 that is on the inside of the curve and an outer region 27 that is on the outside of the curve. The flexible interconnection of adjacent middle-section strut rings 60, described above with reference to FIG. 3, facilitates a longitudinal expansion of stent body 52 along outer region 27 that is greater than a longitudinal expansion along inner region 25. For some applications, the flexible interconnection of adjacent middle-section strut rings 60 facilitates a longitudinal expansion of stent body 52 along outer region 27, and a longitudinal compression of stent body 52 along inner region 25.

For some applications, as shown in FIG. 3, proximal section 54 comprises a proximal-section strut ring 70. Proximal section 54 and middle section 58 are configured such that, when stent body 52 is in the radially compressed configuration thereof (e.g., inside the blood vessel, as described hereinabove), proximal-section strut ring 70 exerts an outward radial force that is greater than an outward radial force exerted by each of middle-section strut rings 60. The greater outward radial force helps proximal section 54 anchor stent 20 in place, as described above with respect to distal section 56. For some applications, as shown in FIG. 3, proximal-section strut ring 70 comprises a plurality of thickened proximal-section struts 72, each thickened strut 72 having a greater cross-sectional area than each of a majority of middle-section struts 62. (In the example shown in FIG. 3, each thickened strut 72 has a greater cross-sectional area than each one of middle-section struts 62.) In such applications, proximal-section strut ring 70 is configured to exert a greater outward radial force by virtue of proximal-section struts 72 being thickened. For some applications, as shown in FIG. 3, each of a majority of thickened proximal-section struts 72 is longer than each of a majority of middle-section struts 62. (In the example shown in FIG. 3, each thickened strut 72 is longer than each of middle-section struts 62.) Typically, the increased length of thickened struts 72 helps reduce strain on proximal section 54 that may result from the increased cross-sectional area of thickened struts 72.

For some applications, as shown in FIG. 3, distal section 56 further comprises second distal-section strut ring 74, ring 74 being coupled to ring 66 in a closed-cell arrangement, i.e., such that each distally-facing v-shaped strut pair 76 of ring 74 is coupled to a proximally-facing v-shaped strut pair of ring 66, such as to form a closed diamond-shaped cell.

For some applications, stent 20 further comprises a plurality of electrode posts 42 coupled to distal-section strut ring 66, the electrode posts being generally as described hereinabove. The apparatus further comprises a plurality of electrodes 22 (FIGS. 2A-B), each of which is coupled to stent 20 by being placed on a respective electrode post 42, as described hereinabove. For some applications, stent 20 is placed within a curved blood vessel, e.g., near the aortic arch, and electrodes 22 are placed in contact with an aortic site in the vicinity of the aortic arch, e.g., as described hereinabove, and/or as described in U.S. Ser. No. 13/210,778 to Dagan (published as US 2012/0035679), U.S. Ser. No. 12/957,799 to Gross (published as US 2011/0137370), and/or U.S. Ser. No. 12/792,227 to Gross (published as US 2010/0305392), all of which applications are incorporated herein by reference. In such applications, it is typically preferred that electrodes 22 along the inside of the curve not move ahead of electrodes 22 along the outside of the curve (or vice-versa), such as to apply the electrodes to the blood vessel at approximately the same longitudinal position. The closed-cell arrangement of distal section 56 typically helps bring the electrodes into contact with the inner wall of the blood vessel at approximately the same longitudinal position, at least due to reduced flexibility of the closed-cell arrangement relative to open-cell arrangements. (Middle section 58, for example, comprises open-cell arrangements of strut pairs 78, in which it is not the case that every distally-facing v-shaped strut pair is coupled to a proximally-facing v-shaped strut pair of an adjacent ring, such as to form a closed diamond-shaped cell, as described hereinbelow. Therefore, the middle section is typically more flexible than distal section 56.) For example, the proximal end of each of the electrodes is brought into contact with the inner wall of the blood vessel, and points of contact that the proximal ends of the electrodes make with the inner wall generally circumscribe a plane, a normal to the plane being generally parallel to a local longitudinal axis of the structure at the points of contact.

For some applications, as shown in FIG. 3, second distal-section strut ring 74 is flexibly coupled to distal-section strut ring 66, such as to facilitate curving of distal section 56. For example, FIG. 3 show rings 66 and 74 coupled by a plurality of flexible junctions 80, which for some applications comprise springs. Junctions 80 facilitate movement of rings 66 and 74 with respect to one another, the movement including movement that is generally transverse to the longitudinal axis of the stent and the blood vessel. The flexible coupling of rings 66 and 74 facilitates the placement of distal section 56 in areas of relatively high curvature, e.g., within the aorta, near the aortic arch.

For some applications, each of antenna posts 46 comprises a proximal portion 82, a distal portion 84, and a compliant junction 85. Proximal portion 82 and distal portion 84 are configured to be generally straight in the absence of any force being applied to antenna post 46. Proximal portion 82 and distal portion 84 are further configured to flex about junction 85, with respect to one another. The flexibility of antenna posts 46 facilitates the placement of the antenna posts in a portion of a blood vessel having relatively high curvature, e.g., within the aorta, near the aortic arch, as described herein. For some applications, compliant junction 85 is shaped to define between 0.5 and 3 sinusoidal waves. For example, the compliant junction may be shaped to define a single sinusoidal wave, as shown in FIG. 3. Alternatively, the compliant junction may be shaped to define 1.5 sinusoidal waves, as described hereinbelow with reference to FIG. 4, or a different number of sinusoidal waves (e.g., 2 waves or 3 waves). For some applications, compliant junction 85 has a different shape that is such as to facilitate flexing of portions 82 and 84 with respect to one another.

As described above, antenna 28 (FIGS. 2A-B) is disposed annularly on the antenna posts, such that the antenna posts separate antenna 28 from the end of stent body 52. In order for transmitter 26 to communicate with antenna 28 via inductive coupling, it is typically desirable that the antenna become fully expanded inside the blood vessel, such that the antenna is in contact with the inner wall of the blood vessel. Nitinol wire 29, which is coupled to the antenna, typically self-expands inside the subject's blood vessel, and causes the gold antenna to expand such that the antenna is in contact with the inner wall of the blood vessel. For some applications, by facilitating flexing of distal portion 84 of post 46 with respect to proximal portion 82 of the post, junction 85 facilitates bending of the distal portion of the post radially outwardly from the outer surface of the stent body. In this manner, even posts that are disposed on inner region 25 (FIG. 1) of the curved portion of the aorta are able to bend such as to at least partially conform with the curvature of the aorta. Since the antenna is coupled (typically, via suturing) to the distal portions of the posts, the bending of the posts is typically such as to facilitate full expansion of the antenna, such that the antenna is brought into contact with the inner wall of the aorta even at inner region 25 of the curved portion of the aorta.

For some applications, at least some of strut rings 60 and 70 are shaped to define an undulating strut ring. For example, FIG. 3 shows each of strut rings 60 and 70 shaped to define an undulating strut ring. Each undulating strut ring comprises a plurality of strut pairs, e.g., a plurality of v-shaped strut pairs 78. Each pair 78 comprises two struts 62 coupled to one another at a respective proximal junction 86 of the undulating ring. Typically, a plurality of bridges 64 couple the undulating rows to each other and to ring 74. For some applications, each bridge 64 couples a first strut pair 78 in a first ring to a second strut pair 78 in an adjacent ring. For example, FIG. 3 shows each bridge 64 coupling a proximal junction 86 of a first strut pair 78 in a first ring to a proximal junction 86 of a second strut pair 78 in an adjacent ring. Each bridge 64 is coupled to the proximal side of the junction of the more distal ring, and to the distal side of the junction of the more proximal ring.

Typically, each proximal junction 86 of a given ring 60 is coupled directly, via a bridge 64, to a proximal junction of exactly one of (a) a strut pair belonging to an adjacent ring that is disposed proximally to the given ring, and (b) a strut pair belonging to an adjacent ring that is disposed distally to the given ring. Such a configuration typically increases flexibility of stent 20, relative to a configuration (not shown) in which one or more proximal junctions 86 are coupled directly to proximal junctions of both (a) and (b). Further typically, as shown in FIG. 3, bridges 64 are disposed between alternating opposing pairs of proximal junctions of a given pair of adjacent rings. Thus, between each pair of bridges 64 there is an opposing pair of proximal junctions to which no bridge is coupled. In this manner, middle section 58 comprises open-cell arrangements of strut pairs 78, in which it is not the case that every distally-facing v-shaped strut pair is coupled to a proximally-facing v-shaped strut pair of an adjacent ring, such as to form a closed diamond-shaped cell.

For some applications, as shown, at least some of bridges 64 comprise a portion 88 that is generally straight and rigid. As stent 20 is longitudinally stretched, portions 88 of bridges 64 facilitate the transmission of tensile force to the respective strut pairs 78 to which they are coupled, and the strut pairs deform in response to the tensile force. For example, for some applications, portions 88 of bridges 64 are configured to at least partially invert v-shaped pairs 78 (i.e., at least partially increase the angle define by the v-shaped pairs), upon stent 20 being longitudinally stretched.

For some applications, at least some of bridges 64 comprise a flexible portion 90, e.g., a sinusoidally-shaped flexible portion 90. As stent 20 is longitudinally stretched, some tensile force may be transferred to flexible portions 90 of bridges 64, and the flexible portions may deform, e.g., stretch, in response thereto. For some applications, flexible portions 90 facilitate the placement of stent 20 in areas of relatively high curvature, e.g., near the aortic arch (e.g., as described hereinabove), by facilitating curving of stent 20.

Figure 4:
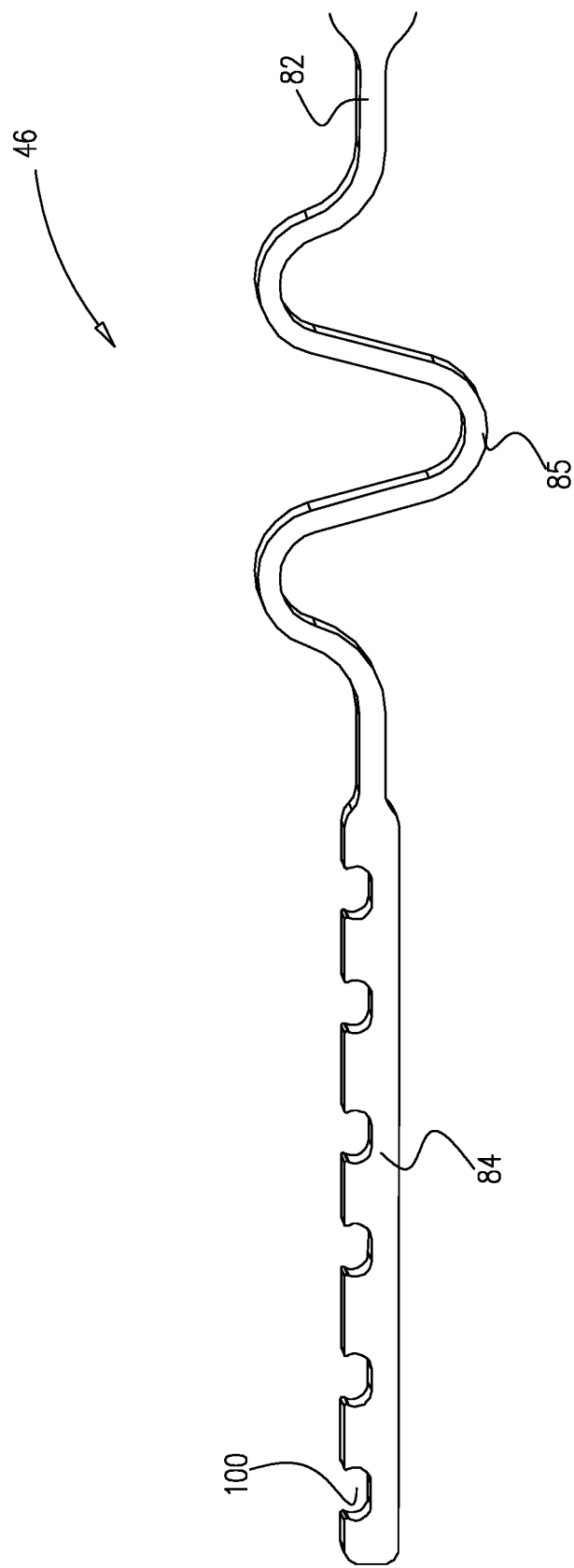
FIG. 4 is a schematic illustration of an antenna post for supporting an antenna, in accordance with some applications of the present invention.

Reference is now made to FIG. 4, which is a schematic illustration of antenna post 46, in accordance with some applications of the present invention. As described hereinabove, for some applications, each of antenna posts 46 comprises a proximal portion 82, a distal portion 84, and a compliant junction 85. As described hereinabove, typically the compliant junction is shaped to define between 0.5 and 3 sinusoidal waves. For example, the compliant junction may be shaped to define a single sinusoidal wave, as shown in FIG. 3. Alternatively, the compliant junction may be shaped to define 1.5 sinusoidal waves, as shown in FIG. 4. For some applications, shaping the junction to define 1.5 sinusoidal waves increases the compliance of the junction relative to if the junction were to define a single sinusoidal wave, as shown in FIG. 3. For some applications, the compliant junction is shaped to define a different number of sinusoidal waves, e.g., 2 or 3 waves. For some applications, compliant junction 85 has a different shape that is such as to facilitate flexing of portions 82 and 84 with respect to one another. As shown in FIG. 4, the distal portions 84 of the antenna posts typically define notches 100, which are configured to facilitate suturing of antenna 28 and nitinol wire 29 (shown in FIGS. 2A-B) to the antenna posts.

Figure 5:
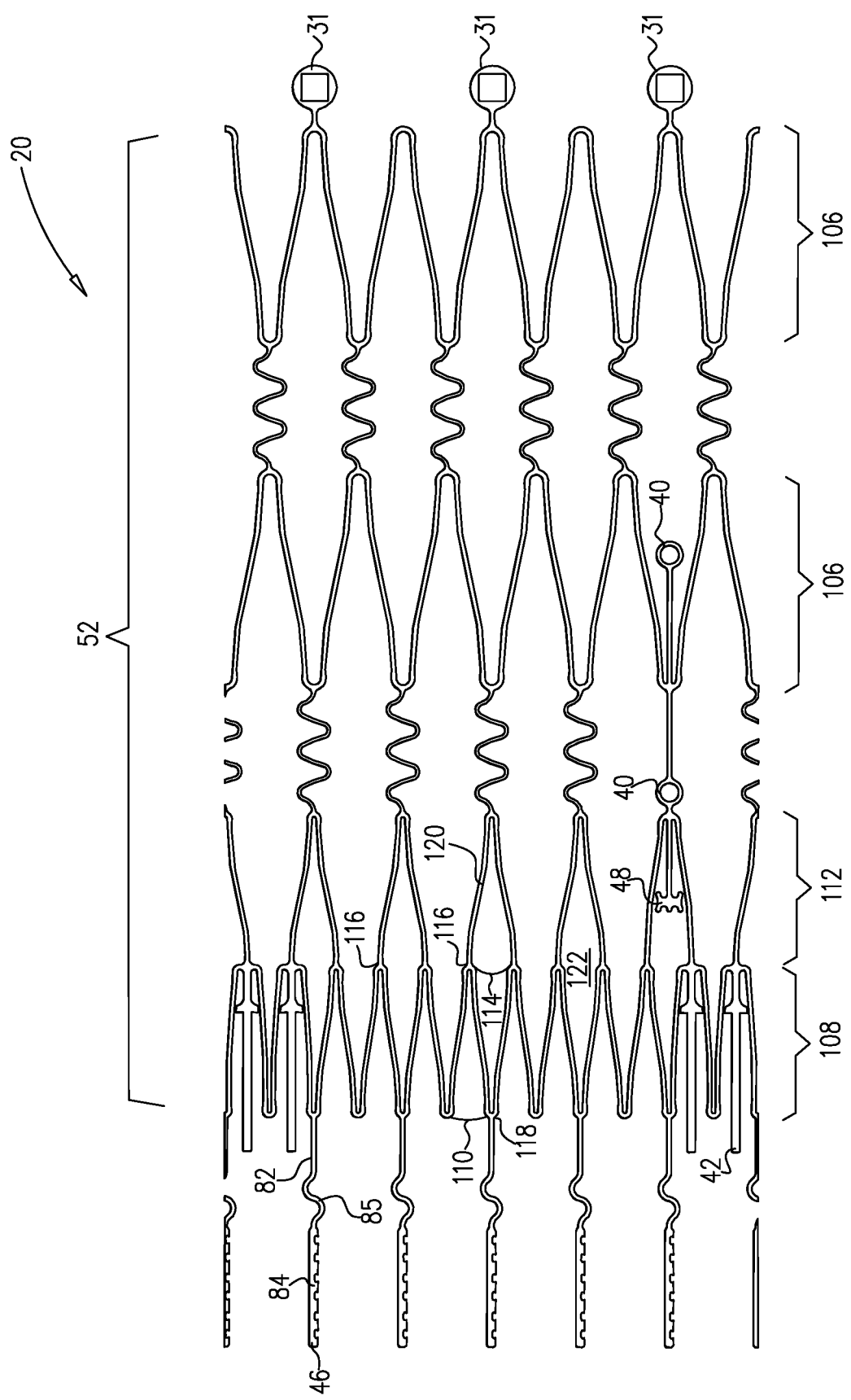
FIG. 5 is a schematic illustration showing the structure of a stent for placing inside a blood vessel, in accordance with some applications of the present invention.

Reference is now made to FIG. 5, which is a schematic illustration of stent 20, in accordance with some applications of the present invention. FIG. 5 shows a flattened profile of the stent, which depicts (for illustrative purposes) how the stent would appear if a longitudinal incision were to be made along the length of the stent at a given circumferential location of the stent, and the stent were to then be laid out flat upon a surface. Stent 20, in accordance with the applications shown in FIG. 5, comprises a generally cylindrical stent body 52 comprising a plurality of undulating strut rings 106. A distal-most undulating strut ring 108 comprises N distal-most-ring v-shaped strut pairs 110. A second undulating strut ring 112 is adjacent to distal-most undulating strut ring 108. Second undulating strut ring 112 comprises N/2 second-strut-ring v-shaped strut pairs 114. For some applications, N is an even integer that is greater than 9 and/or less than 15, e.g., 10-14. For example, FIG. 5 shows an application in which N is 12; thus, FIG. 5 shows 12 distal-most-ring strut pairs 110 and six second-ring strut pairs 114.

Stent 20 further comprises a plurality of antenna posts 46 protruding longitudinally from distal-most undulating strut ring 108, and a plurality of electrode posts 42 protruding from the distal-most undulating strut ring. Stent 20 typically comprises coupling elements 31, as described hereinabove, at a proximal end of the stent. Stent 20 further typically comprises coupling elements 40, as described hereinabove, for facilitating coupling of control capsule 30 to the stent.

For some applications, as shown in FIG. 5, each of distal-most-ring strut pairs 110 comprises two struts coupled at a respective proximal junction 116 of distal-most undulating strut ring 108. Adjacent distal-most-ring strut pairs 110 are coupled to one another at respective distal junctions 118 of distal-most undulating strut ring 108. Each strut 120 of each second-ring strut pair 114 is coupled to a respective proximal junction 116 of distal-most undulating strut ring 108, such as to define N/2 closed-cell arrangements 122 (e.g., N/2 closed diamond-shaped cells). Antenna posts 46 protrude longitudinally from respective distal junctions 118 of distal-most undulating strut ring 108, and electrode posts 42 protrude from respective proximal junctions 116 of distal-most undulating strut ring 108. The configuration of distal-most undulating strut ring 108 and second undulating strut ring 112, as described immediately above, typically helps stabilize the generally distal portion of stent 20. For example, the configuration of distal-most undulating strut ring 108 and second undulating strut ring 112 may help maintain antenna posts 46 and/or electrode posts 42 in a desired orientation (for example, such as to maintain antenna posts 46 and/or electrode posts 42 in alignment with a local longitudinal axis of the stent and/or of the blood vessel).

Typically, antenna 28, electrodes 22, and control capsule 30 are coupled to the stent, as described hereinabove. For some applications, each of electrode posts 42 protrudes from a respective one of a plurality of consecutive proximal junctions 116. For example, FIG. 5 shows four electrode posts 42 protruding from four consecutive proximal junctions 116. For some applications, stent 20 as shown in FIG. 3 is also shaped such that four electrode posts 42 protrude from four consecutive proximal junctions of the distal-most strut ring of the stent body. For some applications, as shown in FIG. 5, the number of antenna posts 46 is N/2, and each of antenna posts 46 protrudes from a respective distal junction 118 such that alternate distal junctions 118 have an antenna post 46 coupled thereto.

For some applications, as described above, N is an even integer that is greater than 9 and/or less than 15, e.g., 10-14. For example, for some applications, N is 12, as shown in FIG. 5. Thus, there are 12 proximal junctions 116, and consecutive electrode posts 42 (and hence, consecutive electrodes 22) are spaced from each other by approximately 1/12 of the circumference of the blood vessel, when stent 20 is an expanded state within the blood vessel.

As described hereinabove, typically, 3-5 electrodes (e.g., 4 electrodes) are coupled to stent 20 such that when the stent is placed inside the subject's aorta, the electrodes are placed in contact with the aorta at an aortic site as described hereinabove, and at circumferential locations that are between the 5 o'clock and the 1 o'clock positions (e.g., between the 7 o'clock and 12 o'clock positions). For some applications, stent 20 defines 3-5 electrode posts 42 (e.g., 4 electrode posts), the electrode posts being disposed around less than 75 percent, e.g., less than 50 percent, or less than 30 percent of the circumference of stent 20. Typically, a spacing of greater than 1/15 and/or less than 1/9 (e.g., 1/15-1/9, e.g., approximately 1/12) of the circumference of the blood vessel is a preferred spacing of electrodes 22 with respect to each other.

Although some applications of the present invention have been described with respect to placing stent 20 inside a subject's aorta, the scope of the present invention includes placing stent 20 inside other blood vessels of a subject's body, e.g., the subject's carotid artery, pulmonary artery, and/or renal artery. For example, the stent may be placed in the renal artery, in order to treat renal dysfunction, and/or in the pulmonary artery, in order to treat pulmonary hypertension. Alternatively or additionally, the stent may be placed in the pulmonary artery and/or the carotid artery in order to be used for vagal stimulation (e.g., vasovagal stimulation), for example, in order to treat gastroesophageal reflux disease (GERD). Similarly, although the stent is shown at least partially disposed in the descending aorta, the scope of the present invention includes placing the stent at any location within the aorta, such as in the ascending aorta, the descending aorta, the aortic arch, or a combination thereof.

For some applications, the subject's cardiac cycle is determined by detecting an electrical signal from the subject's aorta, via electrodes 22, and deriving the subject's ECG and/or blood pressure from the electrical signal detected at the aorta, e.g., in accordance with techniques described in U.S. Ser. No. 12/792,227 to Gross (published as US 2010/0305392). For some applications, physiological parameters of the subject (such as the subject's cardiac cycle) are detecting using antenna 28, for example using techniques as described in US 2014/0180391 to Dagan, which is incorporated herein by reference. For some applications, electrical stimulation is applied to the aorta in coordination with the subject's cardiac cycle, based upon the signal detected at the aorta. For some applications, in response to detecting that a subject is undergoing an epileptic seizure, the subject's vagus nerve is stimulated by driving a current into the subject's aorta. For some applications, a current is driven into the subject's aorta in order to treat the subject for sleep apnea.

It is noted that, although some applications of the present invention have been described as being used in conjunction with a stent, the scope of the present invention includes applying the apparatus and methods described herein to a stent graft, mutatis mutandis. For example, an antenna may be coupled to the body of a stent graft via posts that longitudinally separate the antenna from a distal end of the body of the stent graft, in accordance with the techniques described hereinabove.

For some applications, the techniques described herein are practiced in combination with techniques described in WO 07/013065 to Gross, US 2009/0198097 to Gross, US 2010/0305392 to Gross, US 2011/0137370 to Gross, US 2012/0035679 to Dagan, and/or in US 2014/0180391 to Dagan, all of which applications are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a tubular structure shaped to define a lumen thereof, the apparatus comprising:
   a stent configured to be placed in the lumen, the stent comprising:
      a generally cylindrical stent body comprising a plurality of struts;
      a plurality of electrode posts protruding from the stent body; and
      a plurality of antenna posts protruding longitudinally from an end of the stent body, the antenna posts being longitudinally separated from the electrode posts;
   an antenna disposed annularly on the antenna posts, such that the antenna posts separate the antenna from the end of the stent body; and
   a plurality of electrodes coupled to the stent by being placed on respective electrode posts of the plurality of electrode posts,
   wherein:
      (A)
      the plurality of electrode posts are disposed around less than 75 percent of a circumference of the stent,
      (B)
      the stent defines one or more coupling elements, the apparatus further comprising a control capsule that is configured to:
         be coupled to the stent via the one or more coupling elements,
         receive electrical power from the antenna, and
         drive a current through the plurality of electrodes, using the received electrical power, and
      (C)
      the plurality of electrode posts and the one or more coupling elements are disposed around less than 75 percent of the circumference of the stent, and the one or more coupling elements are rotationally displaced with respect to all of the electrode posts defined by the stent.

2. The apparatus according to claim 1, wherein the lumen of the tubular structure includes a lumen of a blood vessel of a subject, and wherein the stent is configured to be placed inside the lumen of subject's blood vessel.

3. The apparatus according to claim 2, wherein the lumen of the blood vessel includes a lumen of a curved portion of an aorta of the subject, and wherein the stent is configured to be placed inside the lumen of the curved portion of the subject's aorta.

4. The apparatus according to claim 2, wherein the plurality of electrodes are coiled electrodes.

5. The apparatus according to claim 1, wherein the plurality of electrode posts are disposed around less than 50 percent of the circumference of the stent.

6. The apparatus according to claim 5, wherein the plurality of electrode posts are disposed around less than 30 percent of the circumference of the stent.

7. The apparatus according to claim 1, wherein the plurality of electrode posts and the one or more coupling elements are disposed around less than 50 percent of the circumference of the stent.

* * * * *